(12) United States Patent
Min et al.

(10) Patent No.: US 12,194,109 B2
(45) Date of Patent: *Jan. 14, 2025

(54) RADIOACTIVE COMPOUND FOR TREATMENT OF MELANOMA AND USE THEREOF

(71) Applicant: INDUSTRY FOUNDATION OF CHONNAM NATIONAL UNIVERSITY, Gwangju (KR)

(72) Inventors: Jung-Joon Min, Gwangju (KR); Dong-Yeon Kim, Jeollanam-do (KR); A-Young Pyo, Gwangju (KR)

(73) Assignee: INDUSTRY FOUNDATION OF CHONNAM NATIONAL UNIVERSITY, Gwangju (KR)

(*) Notice: Subject to any disclaimer, the term of this patent is extended or adjusted under 35 U.S.C. 154(b) by 868 days.

This patent is subject to a terminal disclaimer.

(21) Appl. No.: 17/134,709

(22) Filed: Dec. 28, 2020

(65) Prior Publication Data

US 2021/0113719 A1 Apr. 22, 2021

Related U.S. Application Data

(63) Continuation of application No. PCT/KR2019/004396, filed on Apr. 11, 2019.

(30) Foreign Application Priority Data

Jun. 28, 2018 (KR) .................. 10-2018-0074766
Apr. 11, 2019 (KR) .................. 10-2019-0042718

(51) Int. Cl.
A61K 51/04 (2006.01)
A61P 35/00 (2006.01)
C07B 59/00 (2006.01)
C07F 5/00 (2006.01)

(52) U.S. Cl.
CPC .......... *A61K 51/0482* (2013.01); *A61P 35/00* (2018.01); *C07B 59/004* (2013.01); *C07F 5/003* (2013.01); *C07B 2200/05* (2013.01)

(58) Field of Classification Search
CPC ............... A61K 51/04; A61K 51/0455; A61K 51/0474; A61K 51/0482
See application file for complete search history.

(56) References Cited

U.S. PATENT DOCUMENTS

2002/0002169 A1* 1/2002 Griffin .................. C07C 43/23
544/380
2007/0202047 A1 8/2007 Wolf

FOREIGN PATENT DOCUMENTS

| DE | 19519508 | | 12/1996 | | |
|---|---|---|---|---|---|
| DE | 19519508 A1 | | 12/1996 | | |
| KR | 1020140117199 | | 6/2016 | | |
| KR | 10-20180083812 | | 7/2018 | | |
| WO | 2008012782 A2 | | 1/2008 | | |
| WO | WO-2009129573 A1 | * | 10/2009 | ......... | A61K 51/0455 |
| WO | WO 2010028281 | * | 3/2010 | | |
| WO | 2018131911 A1 | | 7/2018 | | |

OTHER PUBLICATIONS

Ciaran Nicholl et al., Pharmacokinetics of Iodine-123-IMBA for Melanoma Imaging, J. Nucl. Med, 38, 127-133. (Year: 1997).*

Ivan Greguric et al. Discovery of [18F]N-(2-(Diethylamino)ethyl)-6-fluoronicotinamide: A Melanoma Positron Emission Tomography Imaging Radiotracer with High Tumor to Body Contrast Ratio and Rapid Renal Clearance, J. Med. Chem, 52, 5299-5302. (Year: 2009).*

Hee-Jung Kim et al. Synthesis and characterization of a 68Ga-labeled N-(2-diethylaminoethyl) benzamide derivative as potential PET probe for malignant melanoma, Biorganic & Medicinal Chemistry,20,4915-4920. (Year: 2012).*

Ayoung Pyo et al. "Synthesis and evaluation of radiolabeled protein binder and benzamide derivative for imaging of lung cancer and malignant melanoma" J. Med. Chem. 2013, 56, 895-901.

Liu, et al. "Development of 18F-Labeled Picolinamide Probes for PET Imaging of Malignant Melanoma", Journal of Medicinal Chemistry, 2013, 56, 895-901.

Billaud, et al. "Development and Preliminary Evaluation of TFIB, a New Bimodal Prosthetic Group for Bioactive Molecule Labeling" ACS Med. Chem. Lett. 2015, 6, 168-172.

Dittmann et al. "In Vitro Studies on the Cellular Uptake of Melanoma Imaging Aminoalkyl-Iodobenzamide Derivatives (ABA)" Nuclear Medicine & Biology, vol. 26, pp. 51-56, 1999.

Ren et al. "Melanin-Targeted Preclinical PET Imaging of Melanoma Metastasis" The Journal of Neclear Medicine, vol. 50, No. 10, Oct. 2009.

* cited by examiner

*Primary Examiner* — Michael G. Hartley
*Assistant Examiner* — Jagadishwar R Samala
(74) *Attorney, Agent, or Firm* — Stuart H. Mayer; Kaplan Breyer Schwarz LLP

(57) ABSTRACT

The present invention relates to a radioactive compound with improved targeting ability for melanoma and a pharmaceutical composition for the treating melanoma comprising the same, and the targeting ability for melanoma is improved as compared to the conventional contrast agent for melanoma. The radioactive compound according to an embodiment of the present invention shows a very excellent therapeutic effect on melanoma.

16 Claims, 2 Drawing Sheets

RADIOACTIVE COMPOUND FOR TREATMENT OF MELANOMA AND USE THEREOF

CROSS-REFERENCES TO RELATED APPLICATIONS

This application claims priority to Korean Patent Application No. 2018-0074766 filed Jun. 28, 2018, Korean Patent Application No. 2019-0042718 filed Apr. 11, 2019. In addition, this application is a continuation application of International Application No. PCT/KR2019/004396 filed April 11, and entitled "A radioactive compound for treating melanoma and use thereof", the contents of which are hereby incorporated by reference in their entirety.

TECHNICAL FIELD

The present invention relates to a novel compound and use thereof, and more particularly, to a novel radioactive compound for the treatment of melanoma and use thereof.

BACKGROUND ART

Malignant melanoma is known as one of the most lethal cancers due to its high systemic metastasis. Malignant melanoma accounts for 5% of all skin cancers, but accounts for more than 50% of skin cancer-related deaths. Moreover, the incidence of the disease has doubled over the past two decades and is steadily increasing. Until now, effective treatments for melanoma have not been developed. However, early diagnosis and accurate determination of the stage of the disease have been suggested as an important approach to improving the survival rate of malignant melanoma patients.

Recently, $^{18}$F—N-[2-(diethylamino)ethyl]-4-fluoro-Benzamide ($^{18}$F-FBZA) was developed and reported as a PET contrast agent targeting melanin for the detection of metastatic melanoma (Ren et al., J. Nucl. Med. 50(10): 1692-1699, 2009). However, in the case of the PET contrast agent for melanoma detection, the principle of inducing the selective intake of melanoma by using chemical conversion of the benzamide structure, but the intake rate by melanoma is low and the image quality is poor, thus the problem should be improved. In addition, but until now, the only therapeutic option for melanoma is the surgical removal of the lesion and along with use of anticancer drugs. However, in the case of surgery, not only is there a lot of locational restrictions, but the drug has a disadvantage of the risk of recurrence and the efficiency of treatment response are very low. Therefore, radiotherapy through selective ingestion of radioactive compounds by malignant melanoma is considered to be the most effective, but no effective radiopharmaceutical targeting melanoma has been developed yet.

DISCLOSURE OF THE INVENTION

Technical Problem

The present invention has been derived to solve various problems including the above problems, and an object of the present invention is to provide a novel radioactive therapeutic compound with improved melanoma targeting ability.

Another object of the present invention is to provide a pharmaceutical composition for treating melanoma comprising the compound.

However, these problems are exemplary, and the scope of the present invention is not limited thereto.

Technical Solution

In an aspect of the present invention, there is provided a novel radioactive compound or an acceptable salt thereof having the structure of Formula 1 or 2:

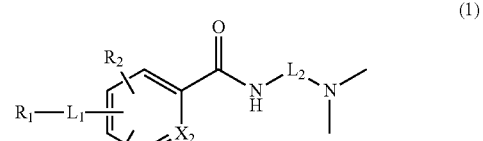

(1)

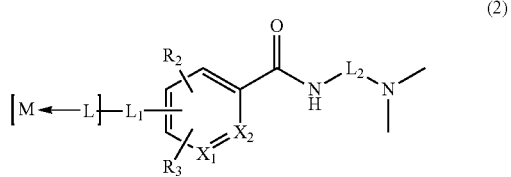

(2)

(In the above formulas, $X_1$ and $X_2$ are each independently carbon or nitrogen; $L_1$ is absent or a bond or a substituted or unsubstituted alkylene having 1 to 20 carbon atoms, a substituted or unsubstituted allyl having 6 to 14 carbon atoms, a substituted or unsubstituted heteroalkylene having 1 to 20 carbon atoms, a (poly)alkylene glycol having 2 to 60 carbon atoms, or one or more functional linkers selected from the group consisting of a hydrophobic moiety for reducing hydrophilicity of the radioactive compound or a pharmaceutically acceptable salt thereof, an albumin-binding moiety for enhancing stability of the radioactive compound or a pharmaceutically acceptable salt and an in vivo clearance promoting moiety for clearing unbound radioactive compounds, which are added modularly; $L_2$ is a bond or a substituted or unsubstituted alkylene group having 1 to 5 carbon atoms; $R_1$ is a radioactive isotope selected from the group consisting of $^{80m}$Br, $^{123}$I, $^{124}$I, $^{125}$I, $^{131}$I, and $^{32}$P or a functional group containing the radioisotope and L is DOTA (1,4,7,10-tetraazacyclododecane-1,4,7,10-tetraacetic acid), DOTA-NCS, DOTA-NHS ester, DOTA-Bz-NCS, tris(t-bu) DOTA, HBED-CC-TFP ester, DTPA (Diethylene triamine penta acetic acid), DO3A (1,4,7,10-tetraazacyclododecane-1,4,7-triacetic acid), NOTA (1,4,7-triazacyclononane-1,4,7-triacetic acid), NODAGA (1,4,7-Triazacyclononane, 1-glutaric acid-4,7-acetic acid), TETA (1,4,8,11-tetraazacyclotetradecane-N,N',N'',N'''-tetraacetic acid), TE3A (1,4,8,11-tetraazacyclotetradecane-1,4,8-triacetic acid), TE2A (1,4,8,11-Tetraazabicyclohexadecane-4,11-diacetic acid), PCTA (3,6,9,15-tetraazabicyclo[9.3.1]pentadeca-1,11,13-triene-3,6,9,-triacetic acid), Cyclen, Cyclam or DFO (Deferrioxamine); M is a radioactive metal selected from the group consisting of $^{64}$Cu, $^{67}$Cu, $^{90}$Cu, $^{68}$Ga, $^{99}$mTc, $^{85}$Sr, $^{89}$Sr, $^{86}$Y, $^{90}$Y, $^{99}$mTc, $^{111}$In, $^{114m}$In, $^{149}$Tb, $^{152}$Tb, $^{153}$Sm, $^{163}$Dy, $^{166}$Ho, $^{169}$Er, $^{177}$Lu, $^{186}$Re, $^{188}$Re, $^{198}$Au, $^{211}$At, $^{212}$Pb, $^{223}$Ra, $^{224}$Ra, $^{225}$Ac and $^{255}$Fm; and $R_2$ and $R_3$ are each independently hydrogen, a hydroxy group, an alkyl group having 1 to 3 carbon atoms, an acetamide group or an alkoxy having 1 to 3 carbon atoms).

According to another aspect of the present invention, there is provided a pharmaceutical composition for treating malignant melanoma comprising said novel radioactive compound or a pharmaceutically acceptable salt thereof as an active ingredient.

In another aspect of the present invention, there is provided a method of treating melanoma in a subject in need thereof administering therapeutically effective amount of said novel radioactive compound or a pharmaceutically acceptable salt thereof.

Advantageous Effects

The novel radioactive compound and a pharmaceutically acceptable salt thereof according to an embodiment of the present invention can be used as a therapeutic for treating melanoma. The radioactive compound according to an embodiment of the present invention not only has an improved targeting ability for melanoma, but also has the advantage of very remarkably inhibiting the growth of melanoma. However, the scope of the present invention is not limited to the above effect.

MODE FOR CARRYING OUT THE INVENTION

Figure 1:
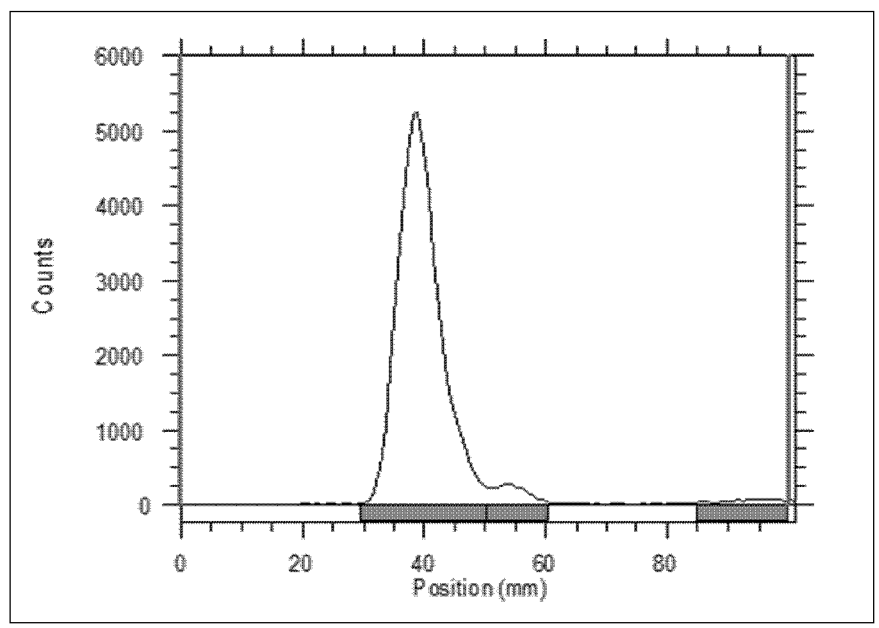
FIG. 1 is a chromatogram showing a result of analyzing a labeling yield and radiochemical purity by separating a radioactive compound according to an embodiment of the present invention by radio thin layer chromatography.

In an aspect of the present invention, there is provided a novel radioactive compound or a pharmaceutically acceptable salt thereof having the structure of Formula 1 or 2:

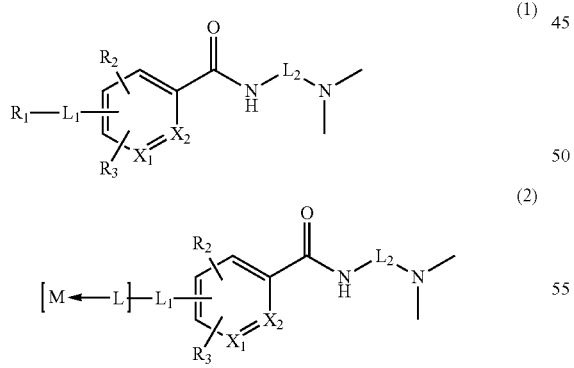

(In the above formulas, $X_1$ and $X_2$ are each independently carbon or nitrogen; $L_1$ is absent or a bond or a substituted or unsubstituted alkylene having 1 to 20 carbon atoms, a substituted or unsubstituted allyl having 6 to 14 carbon atoms, a substituted or unsubstituted heteroalkylene having 1 to 20 carbon atoms, a (poly)alkylene glycol having 2 to 60 carbon atoms, or one or more linkers linked modularly; $L_2$ is a bond or a substituted or unsubstituted alkylene group having 1 to 5 carbon atoms; $R_1$ is a radioactive isotope selected from the group consisting of $^{80m}$Br, $^{123}$I, $^{124}$I, $^{125}$I, $^{131}$I, and $^{32}$P or a functional group containing the radioisotope and L is DOTA (1,4,7,10-tetraazacyclododecane-1,4,7,10-tetraacetic acid), DOTA-NCS, DOTA-NHS ester, DOTA-Bz-NCS, tris(t-bu)DOTA, HBED-CC-TFP ester, DTPA (Diethylene triamine pentaacetic acid), DO3A (1,4,7,10-tetraazacyclododecane-1,4,7-triacetic acid), NOTA (1,4,7-triazacyclononane-1,4,7-triacetic acid), NODAGA (1,4,7-Triazacyclononane, 1-glutaric acid-4,7-acetic acid), TETA (1,4,8,11-tetraazacyclotetradecane-N,N',N'',N'''-tetraacetic acid), TE3A (1,4,8,11-tetraazacyclotetradecane-1,4,8-triacetic acid), TE2A (1,4,8,11-Tetraazabicyclohexadecane-4,11-diacetic acid), PCTA (3,6,9,15-tetraazabicyclo[9.3.1]pentadeca-1,11,13-triene-3,6,9,-triacetic acid), Cyclen, Cyclam or DFO (Deferrioxamine); M is a radioactive metal selected from the group consisting of $^{64}$Cu, $^{67}$Cu, $^{90}$Cu, $^{68}$Ga, $^{99m}$Tc, $^{85}$Sr, $^{89}$Sr, $^{86}$Y, $^{90}$Y, $^{99}$mTc, $^{111}$In, $^{114m}$In, $^{149}$Tb, $^{152}$Tb, $^{153}$Sm, $^{163}$Dy, $^{166}$Ho, $^{169}$Er, $^{177}$Lu, $^{186}$Re, $^{188}$Re, $^{198}$Au, $^{211}$At, $^{212}$Pb, $^{223}$Ra, $^{224}$Ra, $^{225}$Ac and $^{255}$Fm; and $R_2$ and $R_3$ are each independently hydrogen, a hydroxy group, an alkyl group having 1 to 3 carbon atoms, an acetamide group or an alkoxy having 1 to 3 carbon atoms).

In the novel radioactive compound, the linker may be selected from the group consisting of a hydrophobic moiety for reducing hydrophilicity of the radioactive compound or a pharmaceutically acceptable salt thereof, an albumin-binding moiety for enhancing stability of the radioactive compound or a pharmaceutically acceptable salt and an in vivo clearance promoting moiety for clearing unbound radioactive compounds, which are added modularly.

In the radioactive compound or a pharmaceutically acceptable salt thereof, the hydrophobic moiety may be selected from the group consisting of:

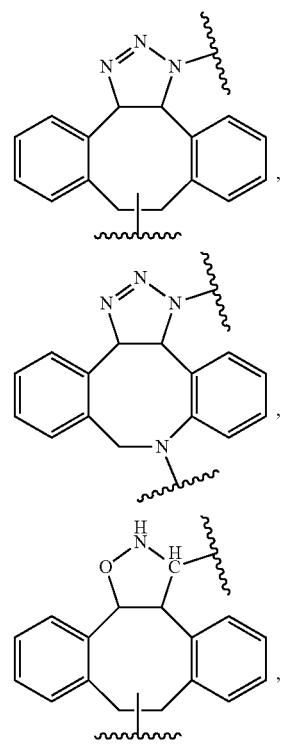

-continued
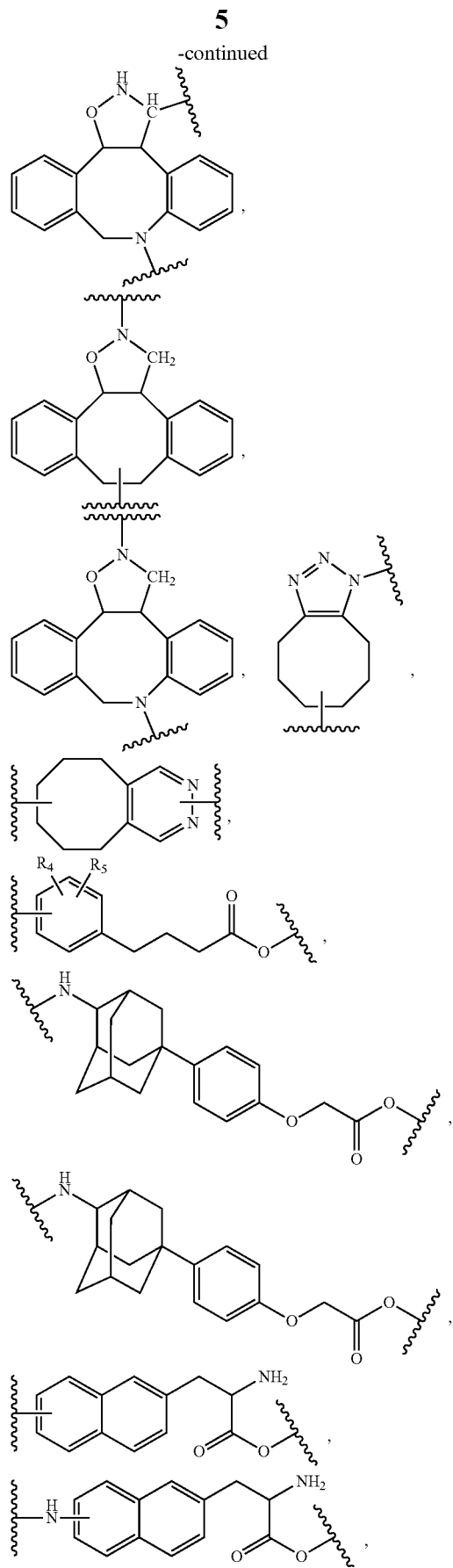
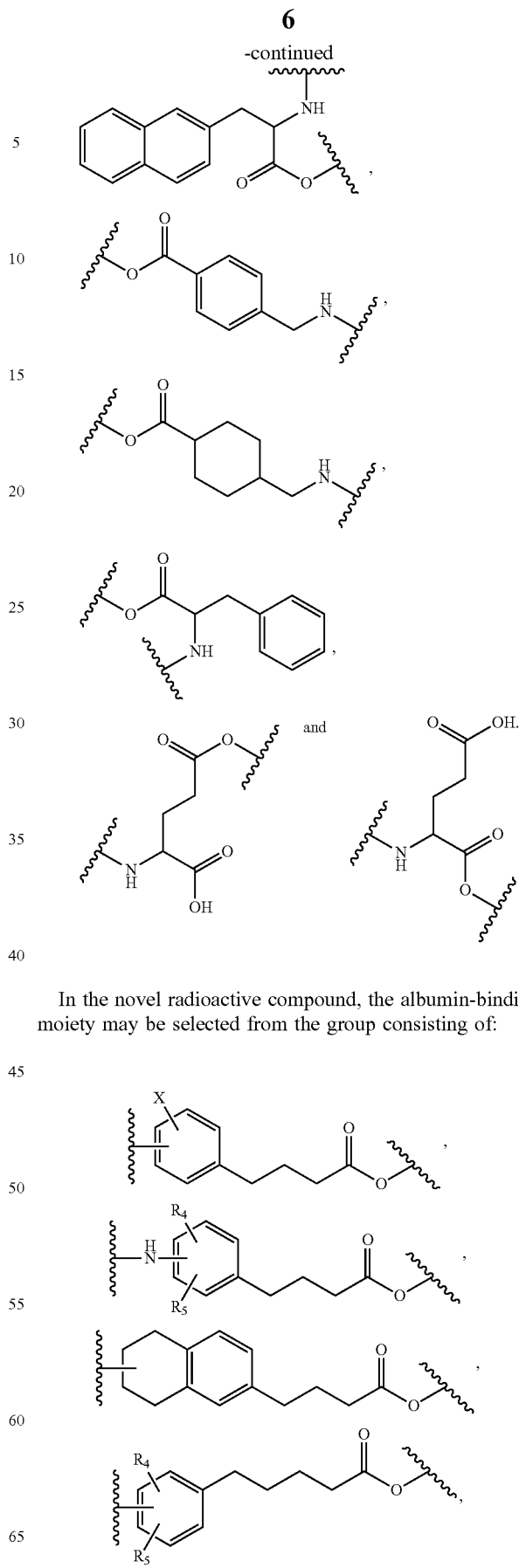
In the novel radioactive compound, the albumin-binding moiety may be selected from the group consisting of:

-continued
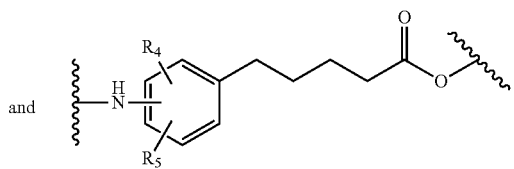
and
(wherein X is a halogen, $R_4$ and $R_5$ are independently hydrogen, hydroxy, or C1 to C6 alkyl or C1 to C6 alkoxy).
Preferably, the albumin-binding moiety may be selected from the group consisting of:
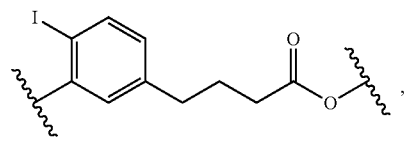
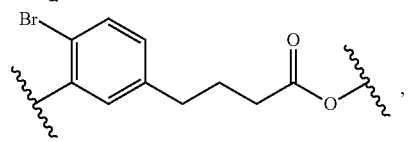
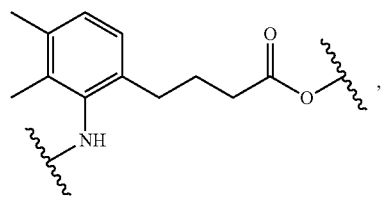
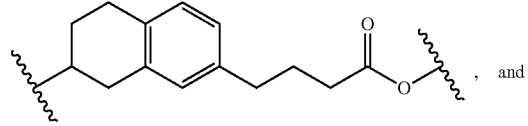
, and
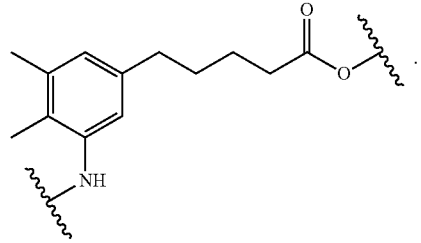
In the novel radioactive compound, the in vivo clearance promoting moiety may be
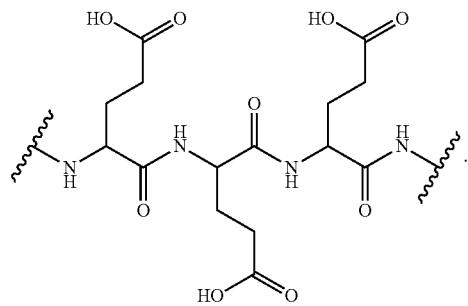 [SMILES: *NC(=O)C(CCC(=O)O)NC(=O)C(CCC(=O)O)NC(=O)C(CCC(=O)O)N*]
Alternatively, the linker may be selected from the group consisting of:
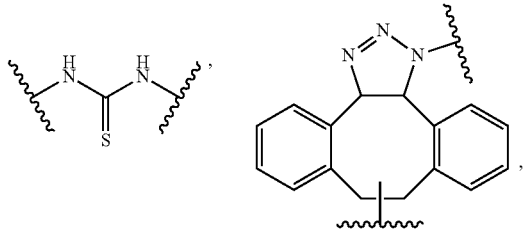
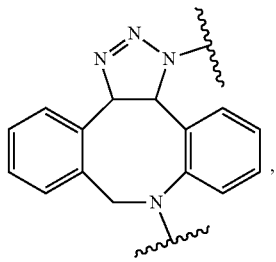
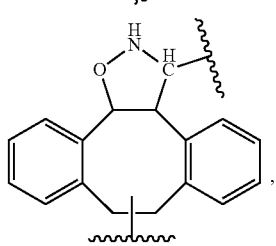
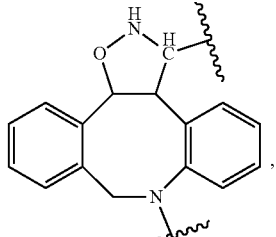
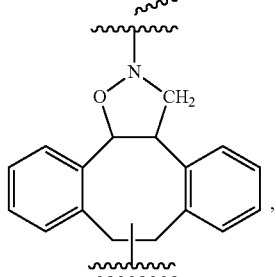
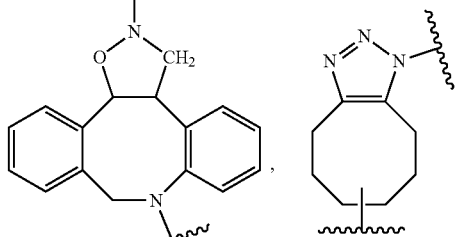
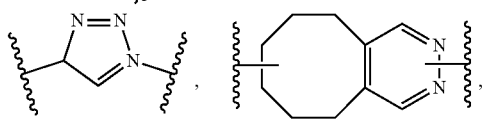

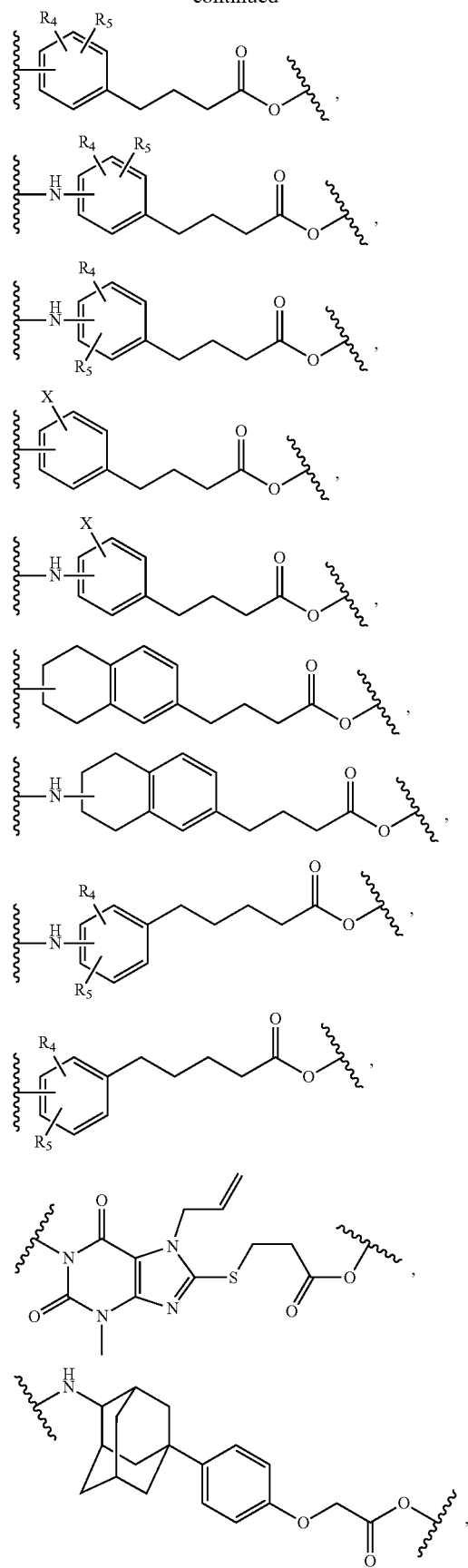
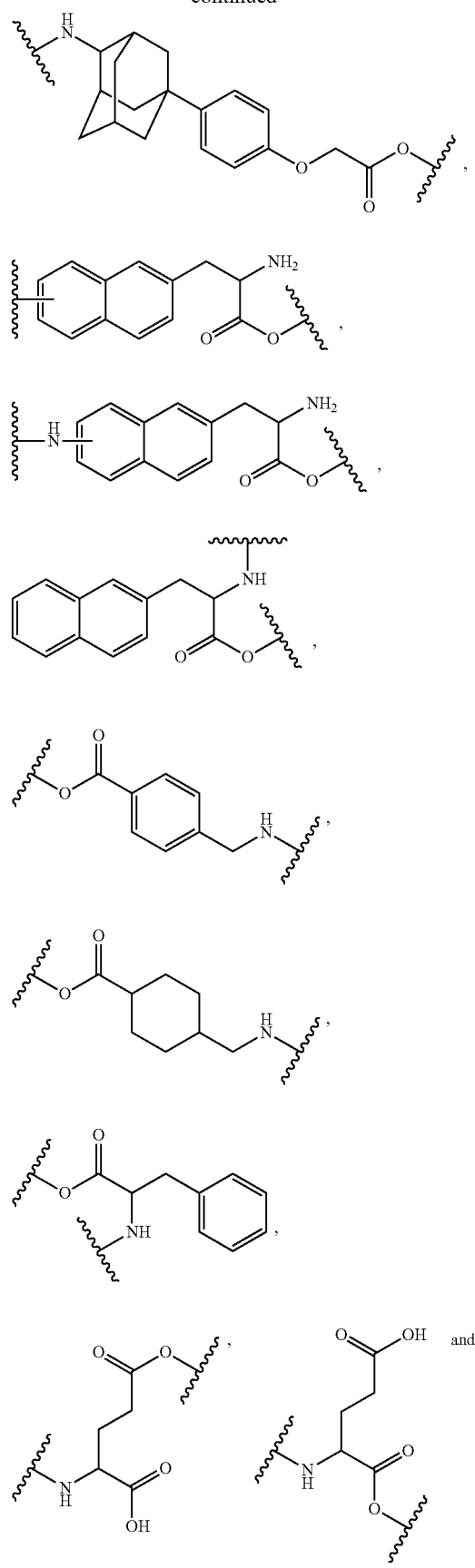

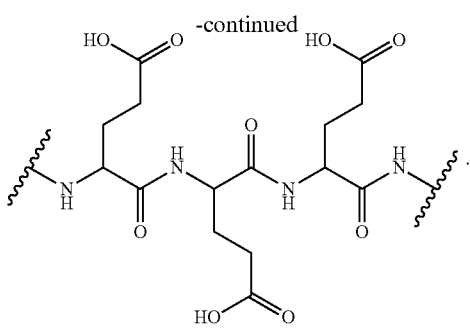

In the novel radioactive compound or a pharmaceutically acceptable salt thereof, the bond may be an ester bond, an amide bond, an ether bond, a thioether bond, a thioester bond, or a disulfide bond, and $L_2$ may be more preferably an alkylene group having 1 to 5 carbon atoms (—$(CH_2)_n$—, n is an integer of 1 to 5), and most preferably an ethylene group (—$CH_2CH_2$—) or a propylene group (—$CH_2CH_2CH_2$—).

According to another aspect of the present invention, there is provided a contrast agent for treating melanoma comprising the compound of Formula 1 or 2 or a pharmaceutically acceptable salt thereof as an active ingredient.

The compound of Formula 1 may be prepared by the following scheme 1:

(Scheme 1)

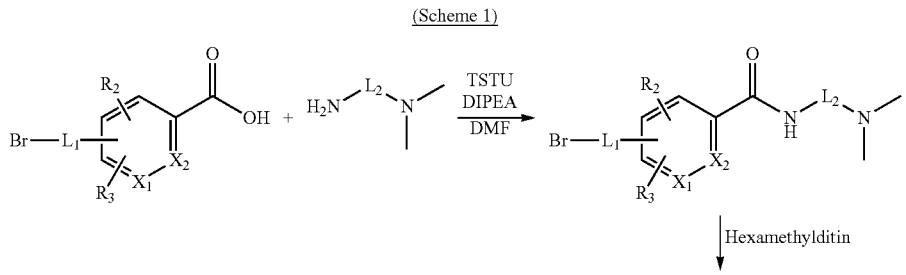

In addition, once the radioactive compound is synthesized one having a general halogen element instead of a radioactive halogen element, $R_1$ may be prepared through a substitution reaction using a salt containing a radioactive halogen element such as $^{80m}Br$ and $^{123}I$. Alternatively, it is also possible to introduce the radioisotope halogen element or radioactive phosphorus by reaction with a compound having the radioisotope halogen element or the radioactive phosphorus as a functional group (eg, phosphoric acid group).

Specific embodiments of the compound or a pharmaceutically acceptable salt thereof are as follows:

(5-((2-(dimethylamino)ethyl)carbamoyl)pyridin-2-yl) carbamic [$^{131}I$] iodide

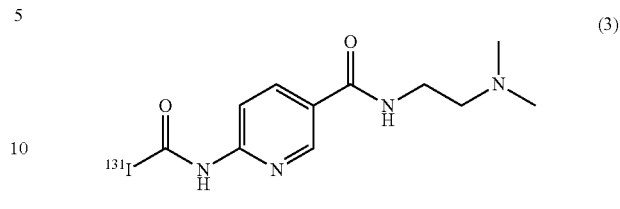

N-(2-(dimethylamino)ethyl)-6-([$^{125}I$] iodomethyl)nicotinamide

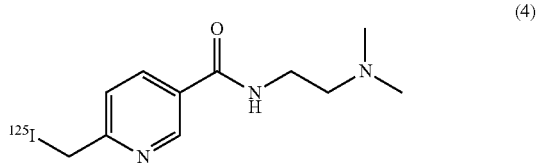 [SMILES: CN(C)CCNC(=O)c1ccc(C[125I])nc1]

N-(2-(dimethylamino)ethyl)-5-([$^{125}I$] iodomethyl)picolinamide

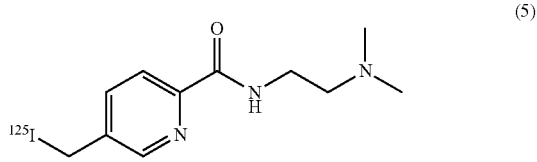 [SMILES: CN(C)CCNC(=O)c1ccc(C[125I])cn1]

N-(3-(dimethylamino)propyl)-5-[$^{131}$I] iodopyridine-2-carboxamide (S)-5-(2-amino-3-(4-hydroxy-3-[$^{131}$I] iodophenyl)propanamido)-N-(2-(dimethylamino)ethyl)picolinamide

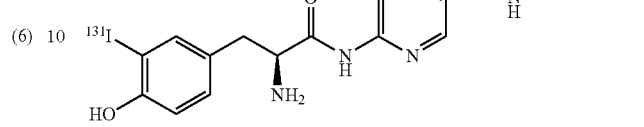
(7)

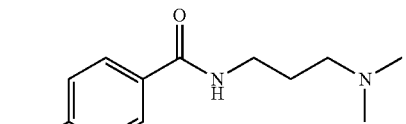
(6)

(S)-5-(4-(4-(2-(2-amino-3-(4-hydroxy-3-[$^{125}$I] iodophenyl)propanamido)ethyl)-1H-1,2,3-triazol-1-yl)butanamido)-N-(2-(dimethylamino)ethyl)picolinamide

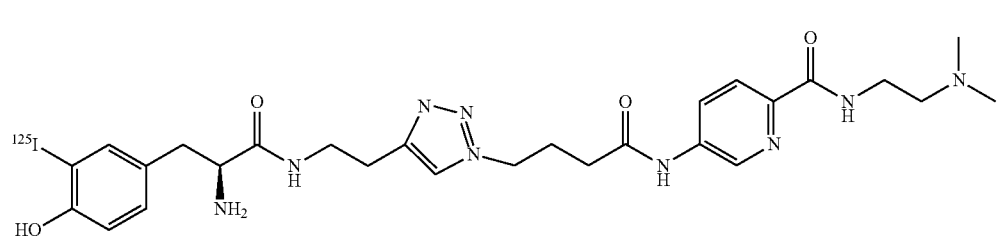
(8)

(S)-6-(6-(3-(3-(2-amino-3-(4-hydroxy-3-[$^{125}$I] iodophenyl)propanamido)propyl)-3H-dibenzo[b,f][1,2,3]triazolo[4,5-d]azocin-8 (9H)-yl)-6-oxohexanamido)-N-(2-(dimethylamino)ethyl)nicotinamide

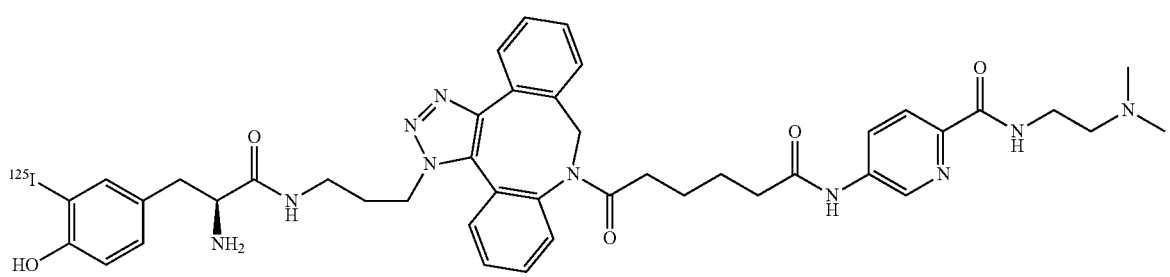
(9)

(6-((2-(dimethylamino)ethyl)carbamoyl)pyridin-3-yl)methyl dihydrogen [$^{32}$P]phosphate)

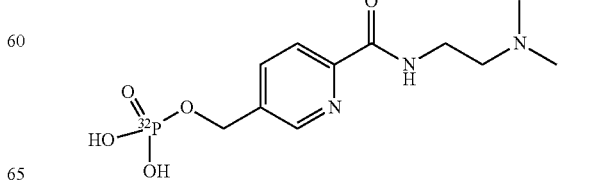
(화학식10)

4-acetamido-N-(2-(dimethylamino)ethyl)-5-[$^{131}$I] iodo-2-methoxybenzamide
(화학식 11)
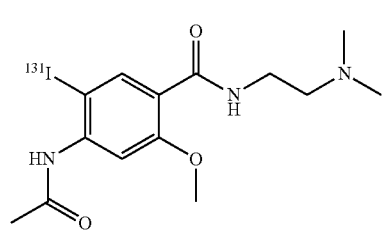
$^{131}$Lu-DOTA-DMP
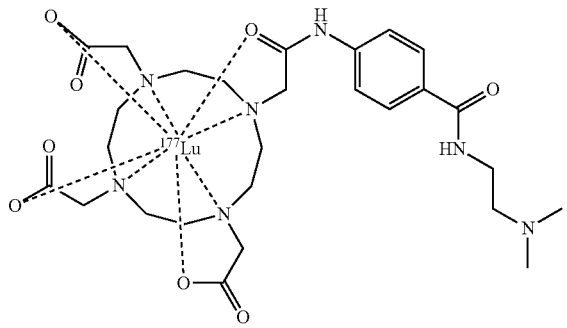
(12)
$^{177}$Lu-DOTA-DMPY2
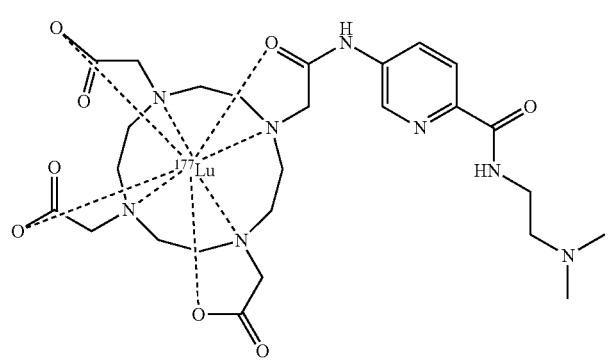
(13)
$^{177}$Lu-DOTA-NCS-DMP
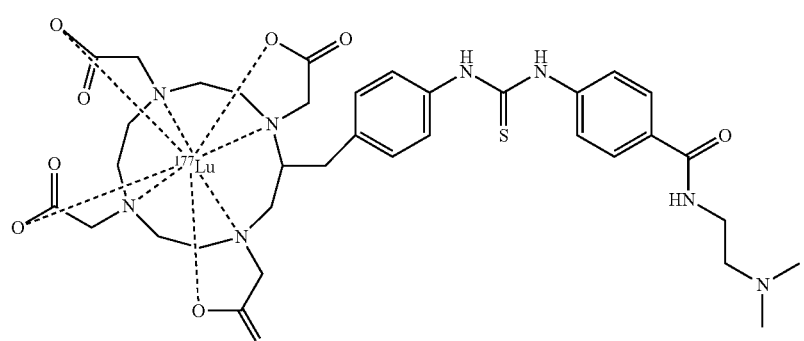
(14)
$^{177}$Lu-DOTA-NCS-DMPY2
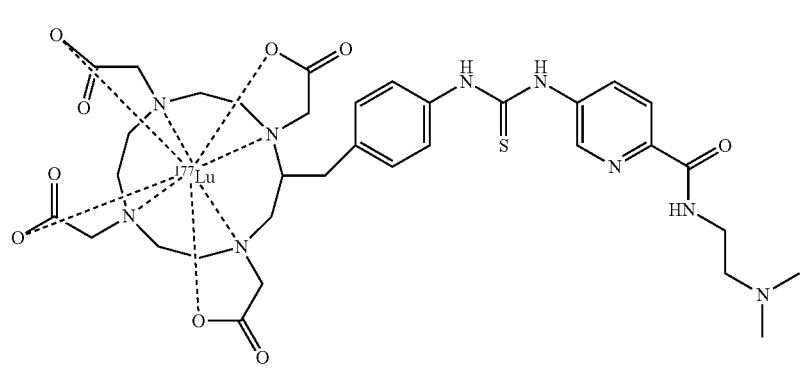
(15)
$^{177}$Lu-DOTA-triazole-PEG-DMP

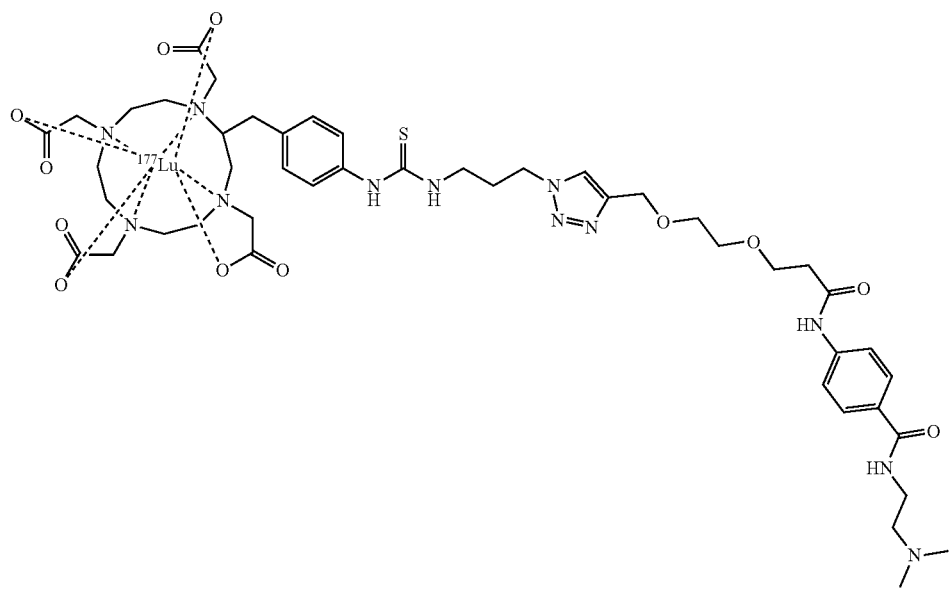
(16)
$^{177}$Lu-DOTA-NCS-triazole-PEG-DMPY2
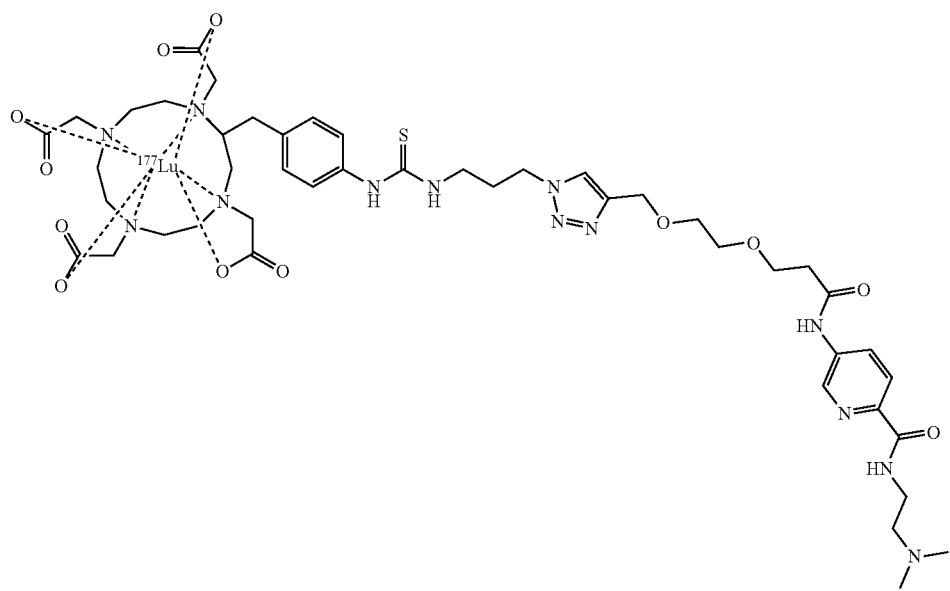
(17)
$^{177}$Lu-DOTA-NCS-ADIBO-DMP

(18)
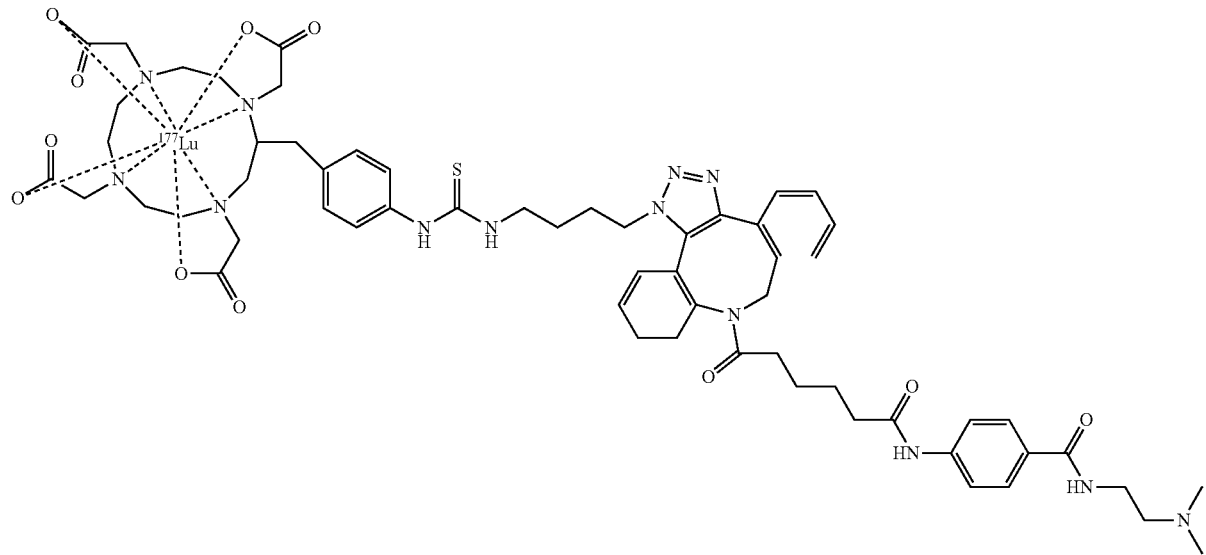
<sup>177</sup>Lu-DOTA-NCS-ADIBO-DMPY2
(19)
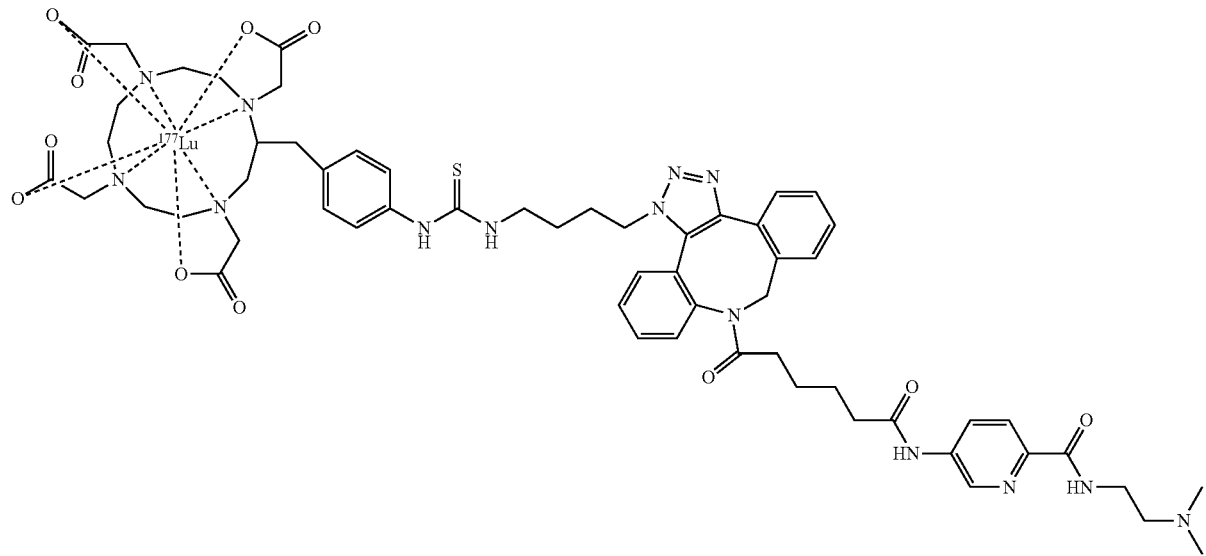
<sup>177</sup>Lu-DOTA-Triazole-DMP -continued
(20)
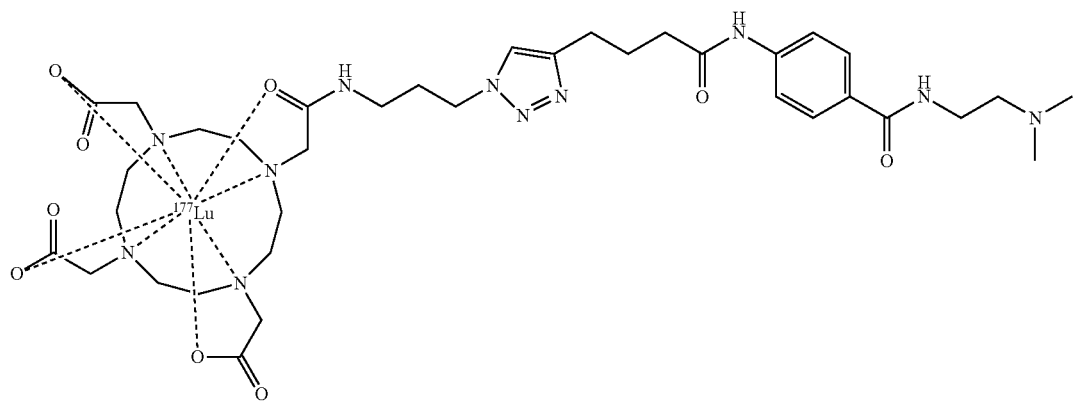
¹⁷⁷Lu-DOTA-Triazole-DMPY2
(21)
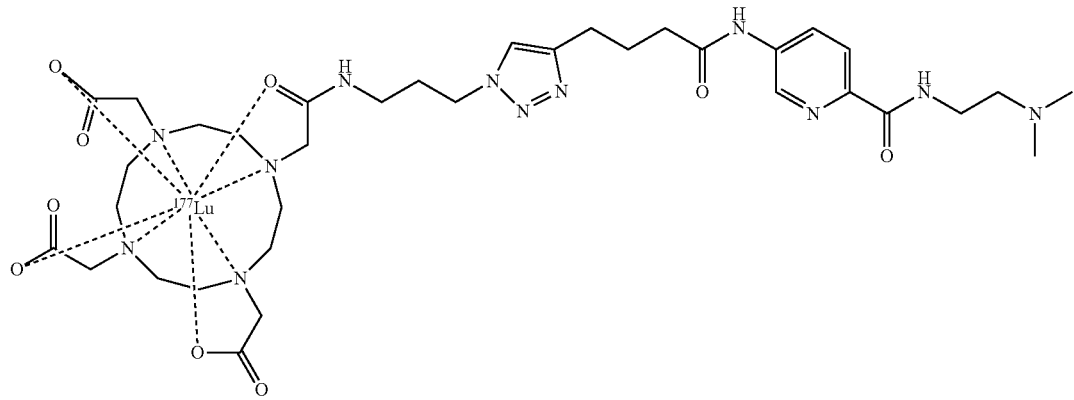
¹⁷⁷Lu-DOTA-Triazole-PEG-DMP
(22)
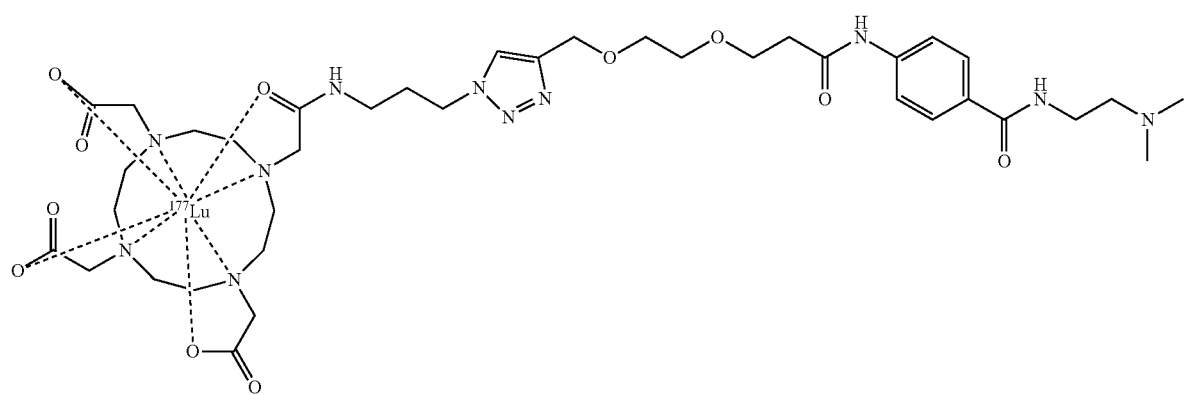
¹⁷⁷Lu-DOTA-Triazole-PEG-DMPY2

-continued

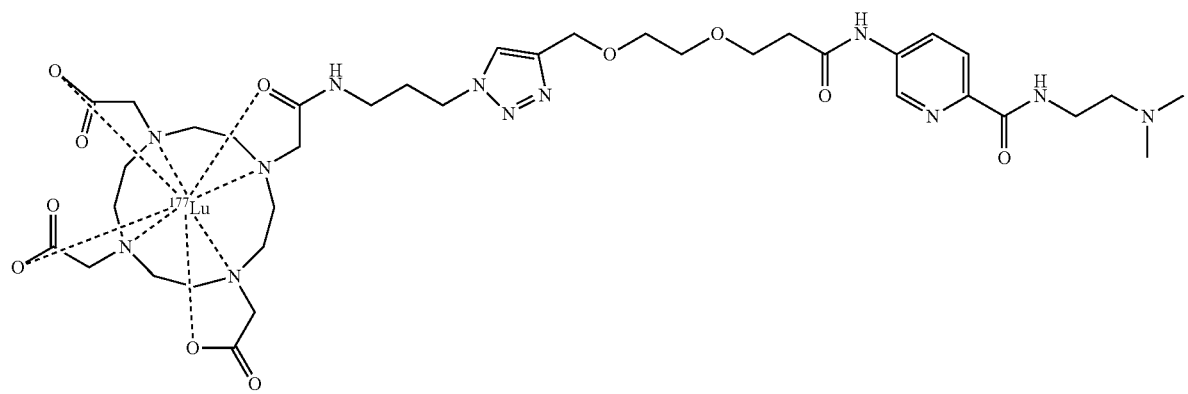

(23)

$^{177}$Lu-DOTA-ADIBO-DMP

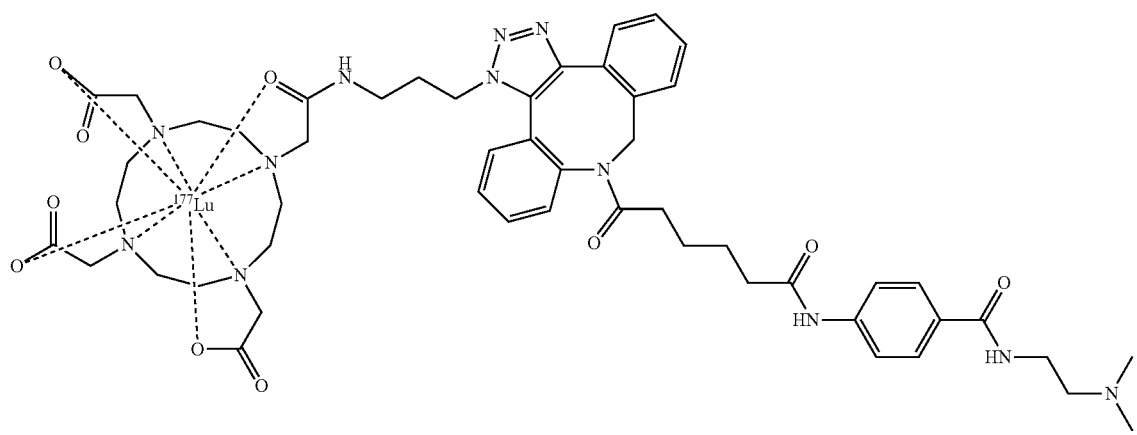

(24)

$^{177}$Lu-DOTA-ADIBO-DMPY2

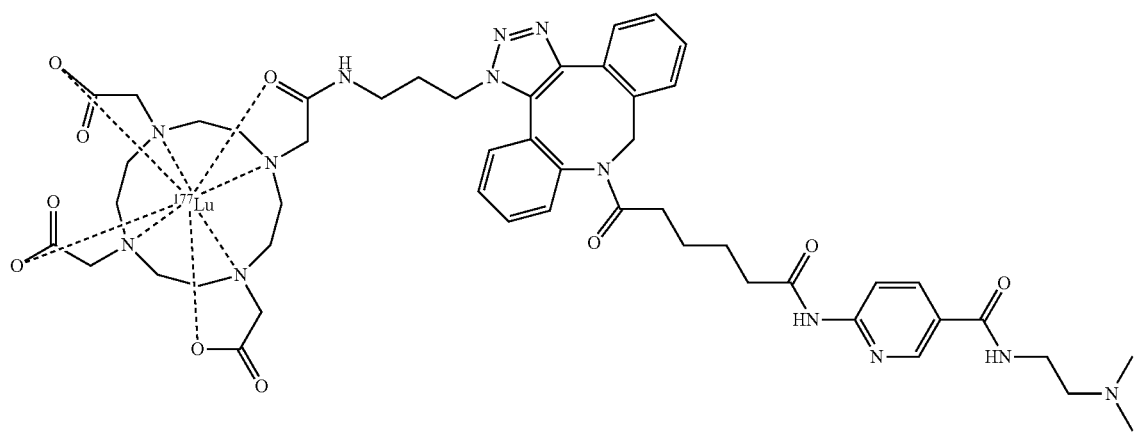

(25)

In the formulas 1 to 25, DOTA is an abbreviation of 1,4,7,10-Tetraazacyclododecane-1,4,7,10-tetraacetic acid, NCS represents isocyanate, PEG is an abbreviation of polyethylene glycol, and DMP is 4-amino-N-(3-(dimethylamino) propyl) benzylamide, DMPY2 is an abbreviation for 6-amino-N-(3-(dimethylamino)propyl)nicotinamide, and ADIBO is an azadibenzocyclooctyne.

In the other hand, the compound of Formula 2 may be prepared by first preparing a chelator-binding compound by a method as shown in Scheme 2 below, and then adding a radioactive isotope metal element thereto:

(Scheme 2).
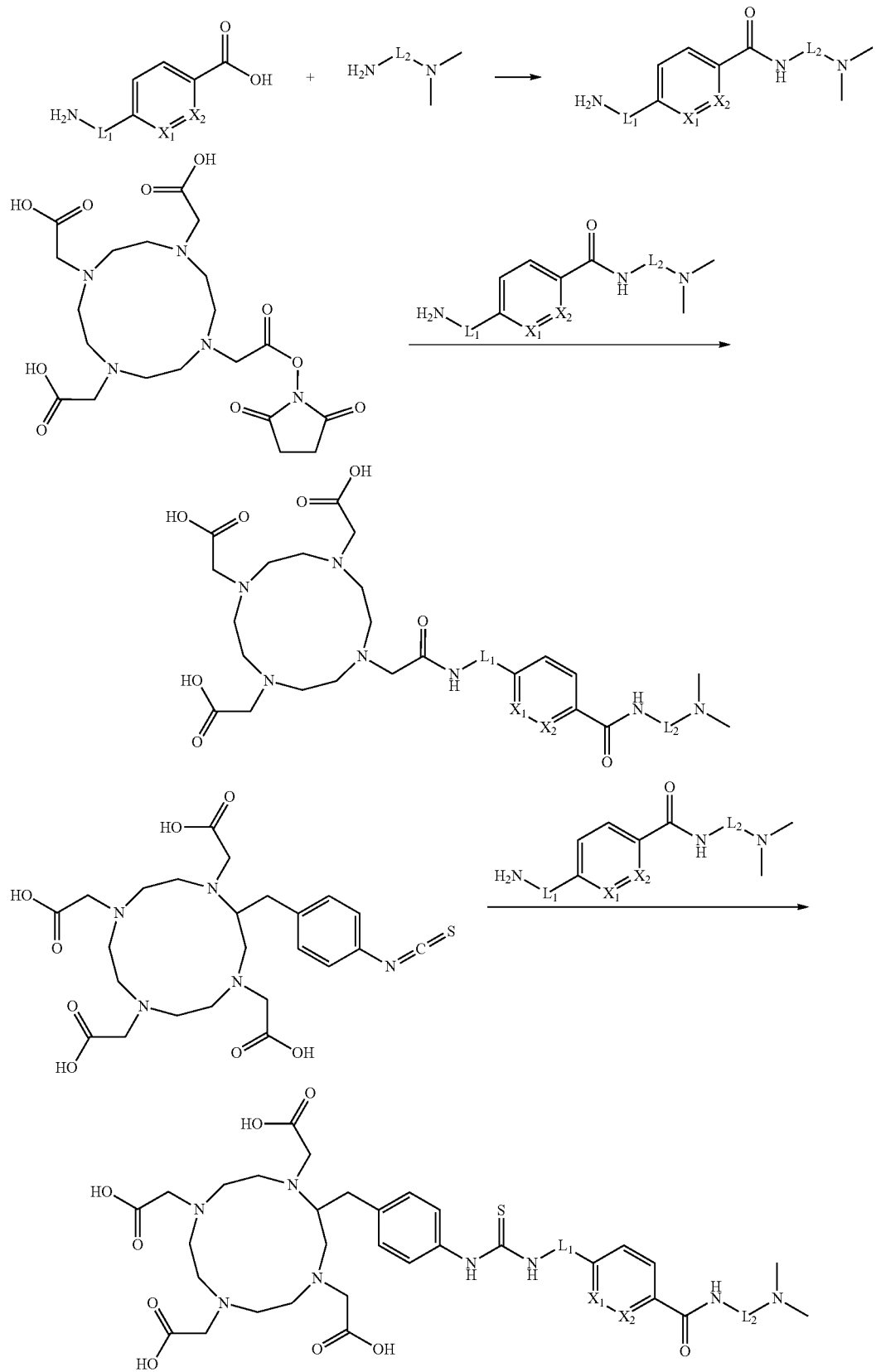

As shown in the above scheme 1, the parent compound can be reacted with hexamethylditine to replace the halogen atom with trimethyltin group, and then reacted with a halogen compound containing a radioactive isotope. At this time, the R1 moiety is a radioisotope moiety, $L_1$ corresponds to a linker connecting the radioisotope moiety and the melanoma targeting moiety, and the right structure excluding the $R_1$ and $L_1$ corresponds to the melanoma targeting moiety. Likewise, as shown in Scheme 2, the chelator moiety can be prepared by being combined with the melanoma targeting moiety, and isothiocyanate (NCS) or the succinimide group, which is a reactive group of the chelator moiety, and amine group of the melanoma targeting moiety may be connected by a thiourea bond or an amide bond, respectively, and the reactive group and the bonding method are exemplary and are not limited to Scheme 2.

In the scheme 1 or 2, the linker $L_1$ may be a modular linker connecting the chelator to the melanoma targeting moiety by click chemistry such as an azide-alkyne cycloaddition reaction, alkyne-nitrone reaction by click chemistry, in addition to general organic synthesis. (alkyne-nitrone cycloaddition) reaction, Alkene and azide [3+2]cycloaddition reaction, Alkene and tetrazine inverse-demand Diels-Alder) reaction, and alkyne and tetrazole photoclick reaction to form triazole or dibenzotriazoloazocine (dibenzotriazoloazocine) besides general organic synthesis. The modular linker may include on or more fungional linkers including a hydrocarbon chain linker ($-[CH_2]_n-$) or polyethylene glycol ($-[C_2H_4O]-$) that serves as a spacer for a certain distance between the radioisotope portion and the melanoma targeting moiety, a hydrophobic moiety (e.g.,

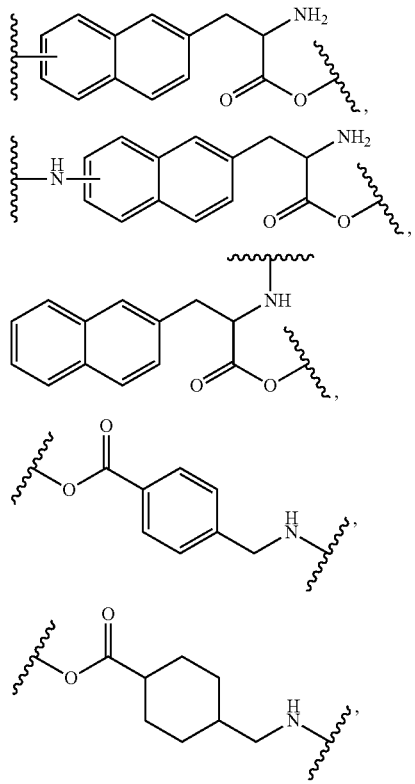

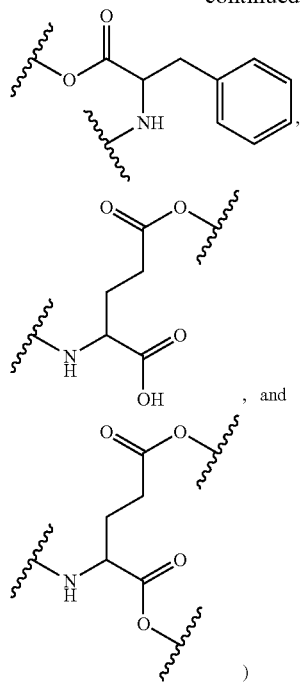

for reducing hydrophilicity of the radioactive compound or the pharmaceutically acceptable salt thereof, or an albumin-binding moiety (e.g.,

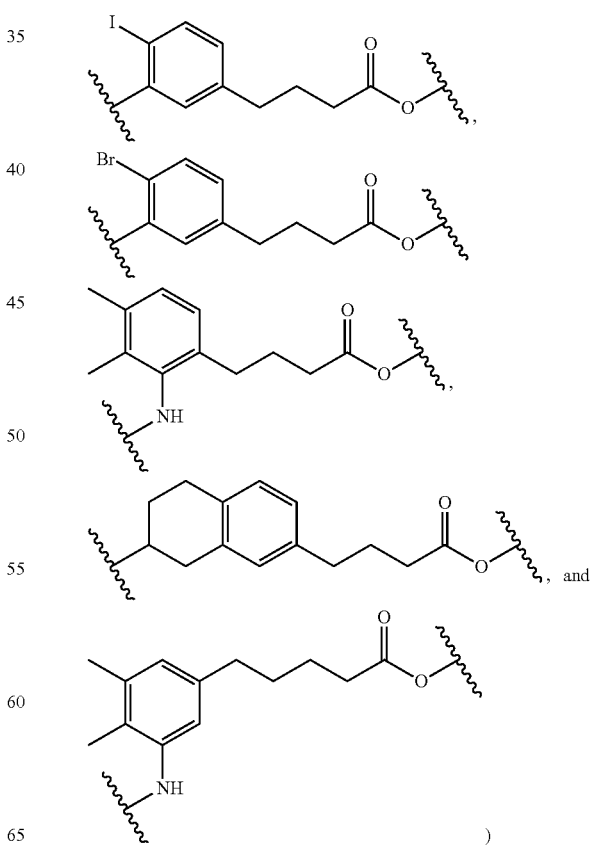

)

for enhancing in vivo stability of the radioactive compound or a pharmaceutically acceptable salt thereof, which are added modularly. In addition, an in vivo clearance enhancing moiety (i.e.,

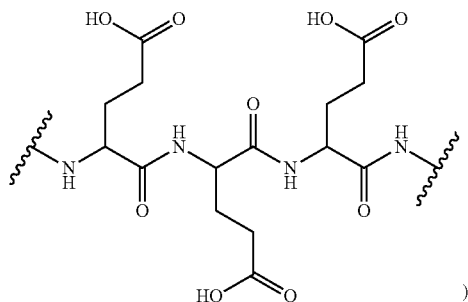 [SMILES: *NC(=O)C(CCC(=O)O)NC(=O)C(CCC(=O)O)NC(=O)C(CCC(=O)O)N*]

)

may be linked between the melanoma targeting moiety and the radioisotope moiety (Huang, S. et al., *The Prostate*, 74(7): 702-713, 2014).

In the novel radioactive compound or a pharmaceutically acceptable salt thereof, the bond may be an ester bond, an amide bond, an ether bond, a thioether bond, a thioester bond, or a disulfide bond, and $L_2$ may be more preferably an alkylene group having 1 to 5 carbon atoms (—$(CH_2)_n$—, n is an integer of 1 to 5), and most preferably an ethylene group (—$CH_2CH_2$—) or a propylene group (—$CH_2CH_2CH_2$—).

The chelators shown in Scheme 2 are exemplary, and various chelators described above may be used.

The "pharmaceutically acceptable salt" is preferably a salt using an inorganic acid or an organic acid, more preferably a salt using an aliphatic such as methoxy, acetoxy, trifluoroacetoxy anion, chloride, bromide, iodide, aromatic or Salts such as aryl aliphatic carboxylate, nitrate, sulfate, phosphate, sulfonate, mesylate, besylate, and tosylate may be used, but are not limited thereto. In addition, the pharmaceutically acceptable salt of the present invention includes salts using $F^-$, $Cl^-$, $Br^-$, or $I^-$. However, the pharmaceutically acceptable salt of the present invention is not limited thereto.

According to another aspect of the present invention, there is provided a pharmaceutical composition for treating melanoma comprising said radioactive compound or a pharmaceutically acceptable salt thereof as an active ingredient.

In practical use, the pharmaceutical composition according to an embodiment of the present invention may be combined with a pharmaceutically acceptable carrier according to conventional pharmaceutical preparation techniques. The carrier may take a wide variety of forms, depending on the preparation desired, for example for oral or parenteral administration (including intravenous administration).

In addition, the pharmaceutical composition according to an embodiment of the present invention may be administered at a dose of 0.1 mg/kg to 1 g/kg, more preferably 0.1 mg/kg to 500 mg/kg. On the other hand, the dosage may be appropriately adjusted according to the age, sex and condition of the patient within the range of the radiation exposure allowed daily or annually.

The pharmaceutical composition according to an embodiment of the present invention further includes an inert ingredient including a pharmaceutically acceptable carrier. As used herein, "a pharmaceutically acceptable carrier" refers to a composition, specifically, a component of a pharmaceutical composition other than an active ingredient. Examples of such pharmaceutically acceptable carriers include binders, disintegrants, diluents, fillers, lubricants, solubilizing or emulsifying agents and salts.

The novel pharmaceutical composition may be administered to the subject by parenteral administration, and the parenteral administration may be intravenous injection, intraperitoneal injection, intramuscular injection, or subcutaneous administration, but intravenous administration is most preferred.

In another aspect of the present invention, there is provided a method of treating melanoma in a subject in need thereof administering therapeutically effective amount of said novel radioactive compound or a pharmaceutically acceptable salt thereof.

Hereinafter, the present invention will be described in more detail through examples and experimental examples. However, the present invention is not limited to the embodiments disclosed below, but may be implemented in various different forms and the embodiments is provide to inform a skilled in the art the scope of the present invention completely.

Example 1: Preparation of Precursors 1-1: Preparation of DOTA-DMP

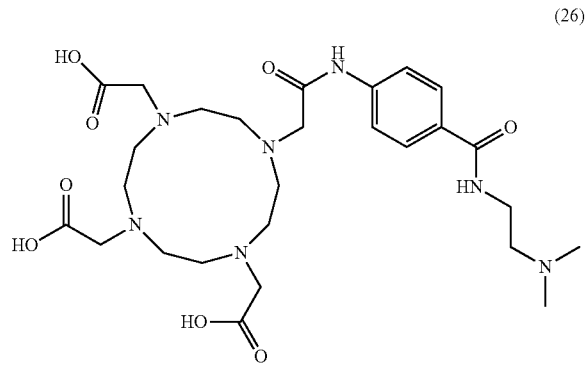 [SMILES: CN(C)CCNC(=O)c1ccc(NC(=O)CN2CCN(CC(=O)O)CCN(CC(=O)O)CCN(CC(=O)O)CC2)cc1]

(26)

5 g of 4-aminobenzoic acid and 0.987 g of N,N,N',N'-tetramethyl-O—(N-succinimidyl)uronium tetrafluoroborate (TSTU) was dissolved in N,N-Dimethylformamide (DMF), and N,N-diisopropylethylamine (DIPEA) 1.72 mL was added and then the mixture was stirred at 60° C. for 3 hours using a reflux device. After stirring for 3 hours, 0.612 ml of N,N-dimethylethylenediamine (DMEDA) was added, followed by stirring at room temperature for 2 hours. The product was extracted with $CH_2Cl_2$ using 60 ml of $CH_2Cl_2$ and 130 ml of $H_2O$, and the moisture of the $CH_2Cl_2$ layer was removed with $MgSO_4$ and filtered. The filtrate was evaporated to dryness, and the product, 4-amino-N-(2-(dimethylamino)ethyl)benzamide, was separated and purified using column chromatography.

Subsequently, 0.08 g of 4-amino-N-(2-(dimethyl-amino) ethyl)benzamide prepared above and 0.229 g of DOTA-NHS ester were dissolved in $CHCl_3$, and the pH was adjusted to 9-10 using triethylamine, and then stirred at room temperature for 24 hours. After removing the solvent by distillation under reduced pressure, 2,2',2"-(10-(2-(4-(2-(dimethyl-amino))ethyl-arbomoyl)phenylamino)-2-oxoethyl)-1,4,7,10-tetraazacyclodode-cane-1,4,7-triyl)triacetic acid having the structure of the above formula 26 was separated using a semi-preparative column and designated as 'DOTA-DMP'. The NMR data are as follows:

$^1$H-NMR (300 MHz, D$_2$O): 2.92 (s, 6H), 3.13 (br, 16H), 3.33 (t, 2H), 3.74 (t, 2H), 3.87 (br, 8H), 6.69 (d, 2H), 7.66 (d, 2H).

1-2: Preparation of DOTA-DMPY2

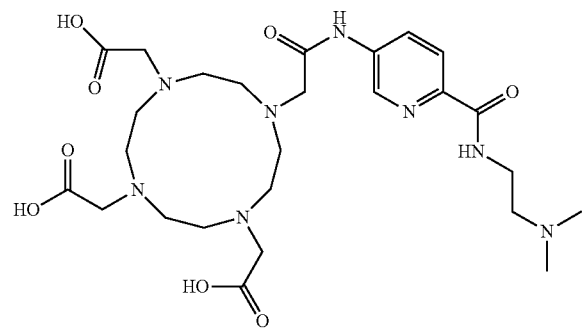

(27)

0.6 g of 5-aminopyridine-2-carboxylic acid and 1.308 g of TSTU were dissolved in DMF, and 2.41 ml of DIPEA was added, followed by stirring at 60° C. for 3 hours using a reflux device. After stirring for 3 hours, 0.808 ml of DMEDA was added, followed by stirring at room temperature for 2 hours. The product was extracted with CH$_2$Cl$_2$ using 80 ml of CH$_2$Cl$_2$ and 130 ml of H$_2$O, and the moisture of the CH$_2$Cl$_2$ layer was removed with MgSO$_4$ and filtered. The filtered filtrate was evaporated to dryness, and 5-amino-N-(2-(dimethylamino) ethyl)picolinamide (NH$_2$-DMPY2) was separated and purified using column chromatography.

Subsequently, 0.07 g of NH$_2$-DMPY2 prepared above and 0.2 g of DOTA-NHS ester were dissolved in CHCl$_3$, the pH was adjusted to 9-10 using triethylamine, and then stirred at room temperature for 24 hours. Subsequently, distillation under reduced pressure to remove the solvent was performed, and then 2,2',2'''-(10-(2-(((6-((2-(dimethylamino) ethyl))carba-moyl)pyridin-3-yl)amino)-2-oxoethyl)-1,4,7,10-tetraazacyclo-dodecane-1,4,7-triyl)triacetic acid having the structure of the above formula 27 was separated using a semi-preparative column and designated as 'DOTA-DMPY2'. $^1$H-NMR analysis results of the DOTA-DMPY2 are as follows:

$^1$H-NMR (300 MHz, D$_2$O): 2.99 (s, 6H), 3.16 (br, 16H), 3.41 (t, 2H), 3.77 (t, 2H), 3.85 (br, 8H), 7.93 (d, 1H), 8.35 (m, 1H), 8.88 (d, 1H).

1-3: Preparation of DOTA-NSC-DMP

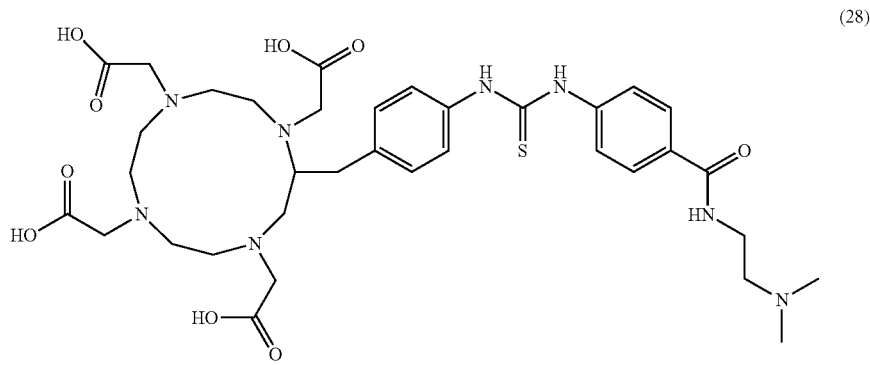 [SMILES: CN(C)CCNC(=O)c1ccc(NC(=S)Nc2ccc(CC3CN(CC(=O)O)CCN(CC(=O)O)CCN(CC(=O)O)CCN3CC(=O)O)cc2)cc1]

(28)

0.08 g of NH$_2$-DMFB prepared in Example 1-1 and 0.208 g of 2-(4-isothiocyanatobenzyl)-1,4,7,10-tetraazacyclodode-cane-1,4,7,10-tetraacetic acid (p-SCN-Bn-DOTA) was dissolved in CHCl$_3$ and the pH was adjusted to 9-10 using triethylamine, followed by stirring at room temperature for 24 hours. After removing the solvent by distillation under reduced pressure, 2,2',2'',2'''-(2-(4-(3-(4-((2-(dimethylamino)ethyl) carbamoyl) phenyl)thioureido)benzyl)-1,4,7,10-tetraaza-cyclododecane-1,4,7,10-tetrayl)tetraacetic acid was separated using a semi-preparative column, and designated as "DOTA-NCS-DMP". 1H-NMR data of the DOTA-NCS-DMP are as follows:

$^1$H-NMR (300 MHz, D$_2$O): 2.92 (s, 6H), 3.13 (br, 16H), 3.33 (t, 2H), 3.74 (t, 2H), 3.87 (br, 8H), 6.43 (d, 2H), 6.69 (d, 2H), 6.86 (d, 2H), 7.66 (d, 2H).

1-4: Preparation of DOTA-NCS-DMPY2

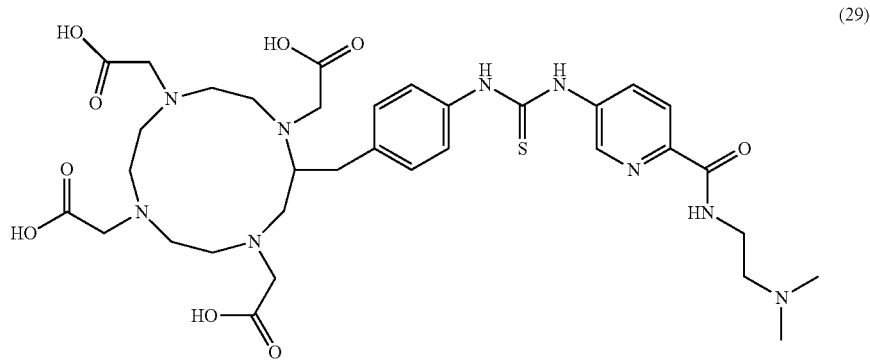 [SMILES: CN(C)CCNC(=O)c1ccc(NC(=S)Nc2ccc(CC3CN(CC(=O)O)CCN(CC(=O)O)CCN(CC(=O)O)CCN3CC(=O)O)cc2)cn1]
(29)

0.07 g of NH$_2$-DMPY2 prepared in Example 1-2 and 0.181 g of p-SCN-Bn-DOTA were dissolved in CHCl$_3$, the pH was adjusted to 9-10 using triethylamine, and then stirred at room temperature for 24 hours. After removing the solvent by distillation under reduced pressure, 2,2',2'',2'''-(2-(4-(3-(6-((2-(dimethylamino)ethyl)carbamoyl)pyridin-3-yl)thioureido) benzyl)-1,4,7,10-tetraaza-cyclododecane-1,4,7,10-tetrayl) tetraacetic acid was separated using a semi-preparative column, and designated as "DOTA-NCS-DMPY2". 1H-NMR data of the DOTA-NCS-DMPY2 are as follows:

$^1$H-NMR (300 MHz, D$_2$O): 2.99 (s, 6H), 3.16 (br, 16H), 3.41 (t, 2H), 3.77 (t, 2H), 3.85 (br, 8H), 6.42 (d, 2H), 6.87 (d, 2H), 7.93 (d, 1H), 8.35 (m, 1H), 8.88 (d, 1H).

Example 2: Preparation of Standard Materials 2-1: Preparation of Lu-DOTA-DMP 5 mg of DOTA-DMP prepared in Example 1-1 and 5 mg of LuCl$_3$ were dissolved in 0.2 M sodium acetate buffer and stirred at 95° C. for 1 hour. Lu-DOTA-DMP having the structure of the above formula 30 was separated using a semi-preparative column. $^1$H-NMR data of the Lu-DOTA-DMP are as follows:

$^1$H-NMR (300 MHz, D$_2$O): 2.94 (s, 6H), 3.12 (br, 16H), 3.34 (t, 2H), 3.72 (t, 2H), 3.85 (br, 8H), 6.68 (d, 2H), 7.65 (d, 2H).

2-2: Preparation of Lu-DOTA-DMPY2

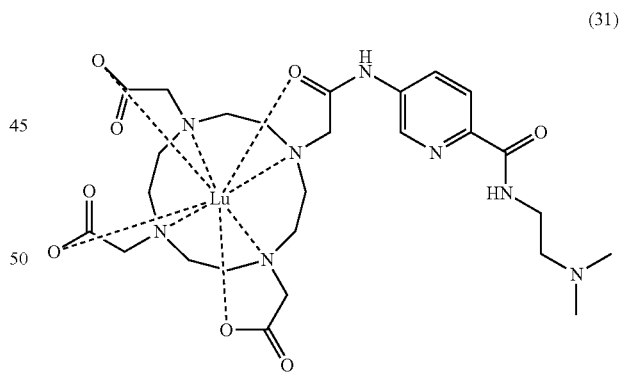
(31)

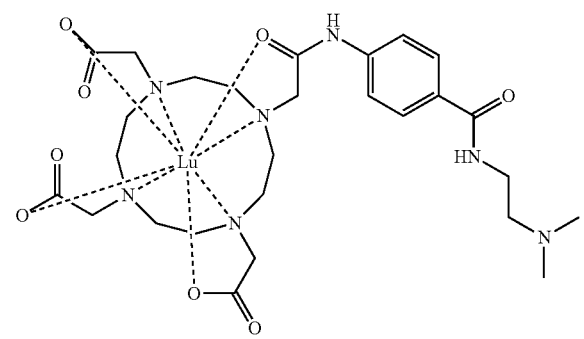
(30)

7 mg of DOTA-DMPY2 prepared in Example 1-2 and 7 mg of LuCl$_3$ were dissolved in 0.2 M sodium acetate buffer and stirred at 95° C. for 1 hour. Lu-DOTA-DMPY2 having the structure of the above formula 31 was separated using a semi-preparative column. $^1$H-NMR data of the Lu-DOTA-DMPY2 are as follows:

1H-NMR (300 MHz, D2O): 2.98 (s, 6H), 3.14 (br, 16H), 3.38 (t, 2H), 3.79 (t, 2H), 3.88 (br, 8H), 7.91 (d, 1H), 8.38 (m, 1H), 8.90 (d, 1H).

2-3: Preparation of Lu-DOTA-NCS-DMP

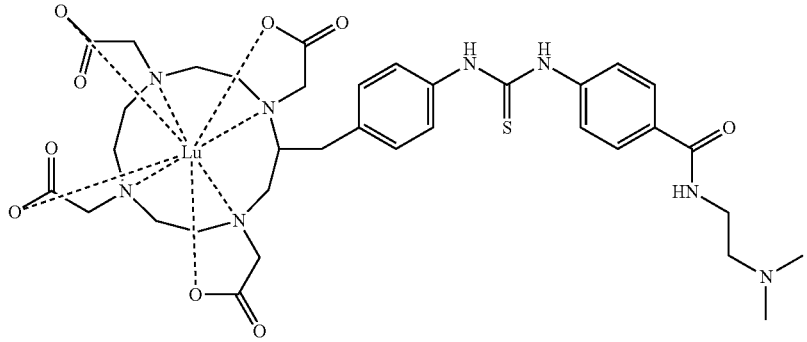

(32)

5 mg of DOTA-NCS-DMP prepared in Example 1-3 and 4 mg of LuCl$_3$ were dissolved in 0.2 M sodium acetate buffer and stirred at 95° C. for 1 hour. Lu-DOTA-NCS-DMP having the structure of above formula 32 was separated using a semi-preparative column. $^1$H-NMR data of the Lu-DOTA-NCS-DMP are as follows:

$^1$H-NMR (300 MHz, D$_2$O): 2.94 (s, 6H), 3.12 (br, 16H), 3.34 (t, 2H), 3.72 (t, 2H), 3.85 (br, 8H), 6.45 (d, 2H), 6.68 (d, 2H), 6.85 (d, 2H), 7.65 (d, 2H).

2-4: Preparation of Lu-DOTA-NCS-DMPY2

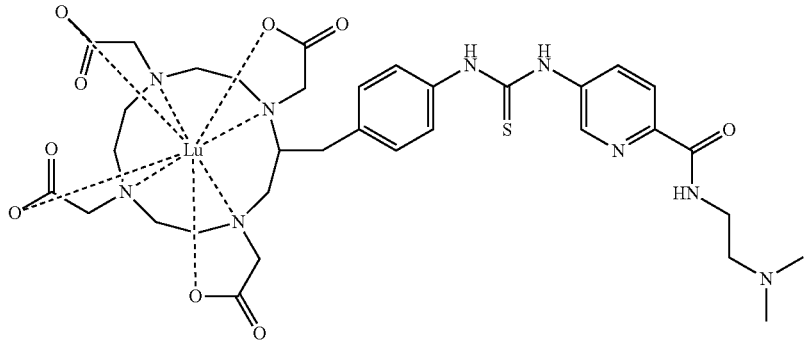

(33)

7 mg of DOTA-NCS-DMPY2 prepared in Example 1-4 and 6 mg of LuCl$_3$ were dissolved in a 0.2 M sodium acetate buffer solution and stirred at 95° C. for 1 hour. Lu-DOTA-NCS-DMPY2 having the structure of above formula 33 was separated using a semi-preparative column. $^1$H-NMR data of the Lu-DOTA-NCS-DMPY2 are as follows:

$^1$H-NMR (300 MHz, D$_2$O): 2.98 (s, 6H), 3.14 (br, 16H), 3.38 (t, 2H), 3.79 (t, 2H), 3.88 (br, 8H), 6.43 (d, 2H), 6.89 (d, 2H), 7.91 (d, 1H), 8.38 (m, 1H), 8.90 (d, 1H).

Example 3: Preparation of Radioactive Compounds

3-1: Preparation of $^{177}$Lu-DOTA-DMP

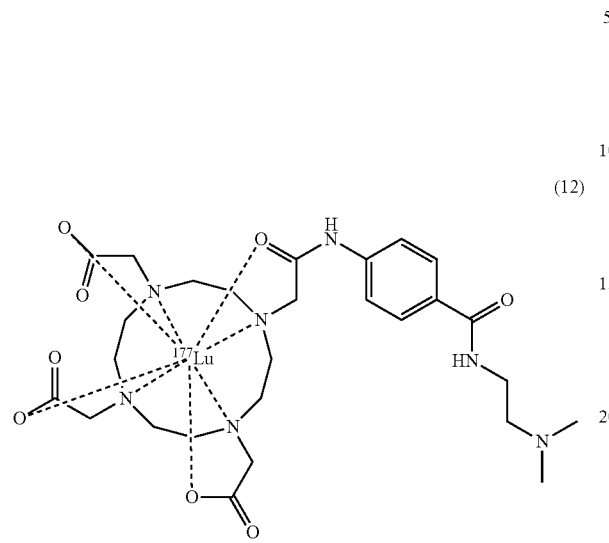

(12)

After dissolving 30 μg of DOTA-DMP prepared in Example 1-1 and $^{177}$LuCl$_3$ (20 mCi) in 0.2 M sodium acetate buffer solution, the reaction mixture was incubated at 90° C. for 1 hour in order to synthesize $^{177}$Lu-DOTA-DMP having the structure of above formula 12. After cooling the reaction mixture at room temperature, the radioactive compound was separated and purified using a semi-preparative column.

3-2: Preparation of $^{177}$Lu-DOTA-DMPY2

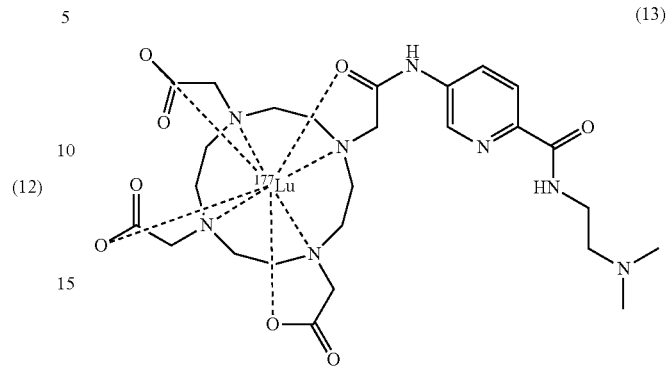

(13)

After dissolving 30 μg of DOTA-DMPY2 prepared in Example 1-2 and $^{177}$LuCl$_3$ (30 mCi) in 0.2 M sodium acetate buffer solution, the reaction mixture was incubated at 90° C. for 1 hour in order to synthesize $^{177}$Lu-DOTA-DMPY2 having the structure of above formula 13. After cooling the reaction mixture at room temperature, the radioactive compound was separated and purified using a semi-preparative column.

As described above, $^{177}$Lu-DOTA-DMPY2 labeled with the radioactive isotope ruthenium $^{177}$Lu was separated by radio thin layer chromatography using an aqueous citric acid solution as a developing solvent to analyze the labeling yield and radiochemical purity. As shown in FIG. 1, the peak appearing between the development distance 20-40 mm represents $^{177}$Lu-DOTA-DMPY2 synthesized by an embodiment of the present invention, and the peak appearing between the development distance 85-95 mm represents non-labeled free $^{177}$Lu. As a result of calculating the area of the peak, it was confirmed that the radiochemical purity of $^{177}$Lu-DOTA-DMPY2 synthesized above was >98% or more.

3-3: Preparation of $^{177}$Lu-DOTA-NCS-DMP

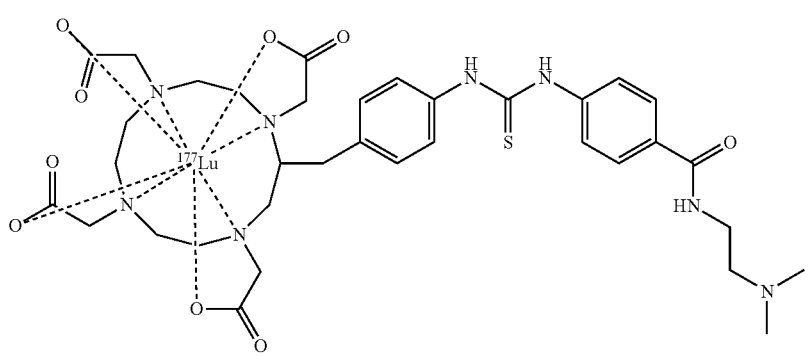

(14)

After dissolving 30 μg of DOTA-NCS-DMP prepared in Example 1-3 and $^{177}$LuCl$_3$ (25 mCi) in a 0.2 M sodium acetate buffer solution, the reaction mixture was incubated at 90° C. for 1 hour in order to synthesize $^{177}$Lu-DOTA-NCS-DMP having the structure of above formula 14. After cooling the reaction mixture at room temperature, $^{177}$Lu-DOTA-NCS-DMP was separated and purified using a semi-preparative column.

3-4: Preparation of $^{177}$Lu-DOTA-NCS-DMPY2

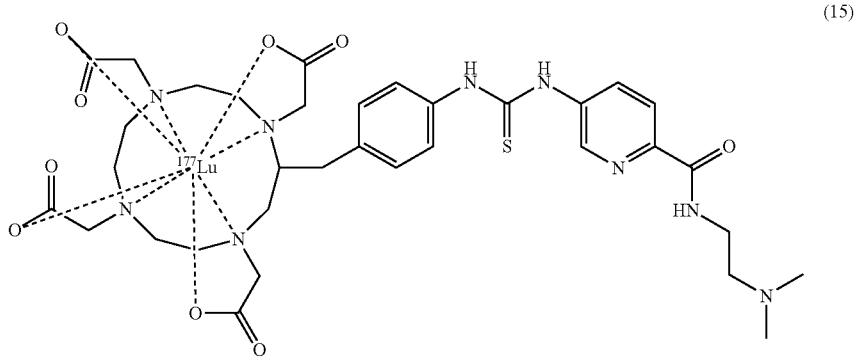

(15)

30 µg of DOTA-NCS-DMPY2 prepared in Example 1-4 and [177]LuCl₃ (23 mCi) were dissolved in a 0.2 M sodium acetate buffer solution, and then the reaction mixture was incubated at 90° C. for 1 hour in order to synthesize $^{177}$Lu-DOTA-NCS-DMPY2 having the structure of above formula 15. After cooling the reaction mixture at room temperature, $^{177}$Lu-DOTA-NCS-DMPY2 was separated and purified using a semi-preparative column.

Experimental Example 1: In Vivo Anti-Cancer Activity Assay

The present inventors administered the radioactive compound prepared in Example 3-4 to the melanoma mouse model intravenously, and measured changes in tumor volume and body weight over time.

Particularly, male BALB/c nu/nu mice (6 weeks old) were used and maintained at the facility of Hwasun Hospital, Chonnam National University College of Medicine. This study protocol was approved by the Institutional Animal Care and Use Committee (IACUC) of Chonnam National University School of Medicine.

The male BALB/c nu/nu mice were inoculated with 1×10⁶ cells of the B16F10 cell line, a mouse melanoma cell line, on the right shoulder. After the tumor volume grew to about 100 to 150 mm³ and stabilized, the $^{177}$Lu-DOTA-NCS-DMPY2 synthesized in Example 3-4 was intravenously injected into the experimental animals at the radiation dose of 90 MBq or 120 MBq, and as a control group, a phosphate buffer solution Only (PBS) was administered. The tumor volume (mm³) and the body weight of the animals were recorded at intervals of 3 days after drug administration until the 21$^{st}$ day, and the tumor volume was calculated using the following calculation formula after measuring the width and length of the tumor tissue:

Tumor volume (mm³)=(width)²×(length)×0.5

The radioactive compound was administered only once at the start of treatment. After the experiment was completed, the experimental animals were sacrificed, the tumor tissues were excised and the weight was measured.

Figure 2:
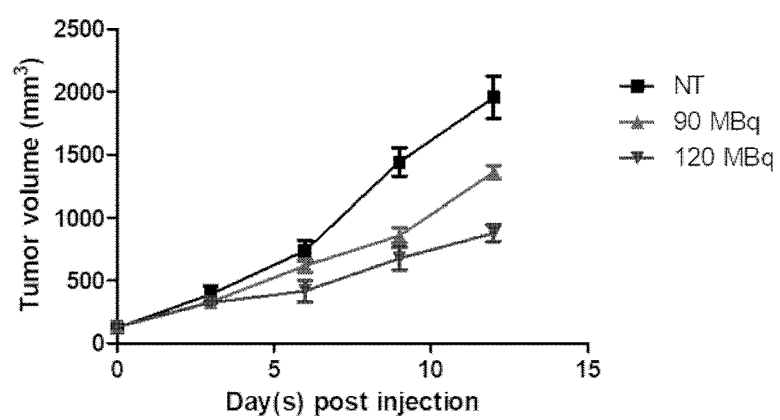
FIG. 2 is a graph showing changes in tumor growth over time when $^{177}$Lu-DOTA-NCS-DMPY2 according to an embodiment of the present invention was administered to a melanoma small animal model.

As a result, as shown in FIG. 2, in the experimental animal administered with $^{177}$Lu-DOTA-NCS-DMPY2 according to an embodiment of the present invention, the size of the tumor was significantly reduced, and in particular, when the radiation dose was doubled, it was confirmed that the tumor almost did not grew.

In addition, in order to check whether the test drug has side effects, the body weights of the experimental animals.

Figure 3:
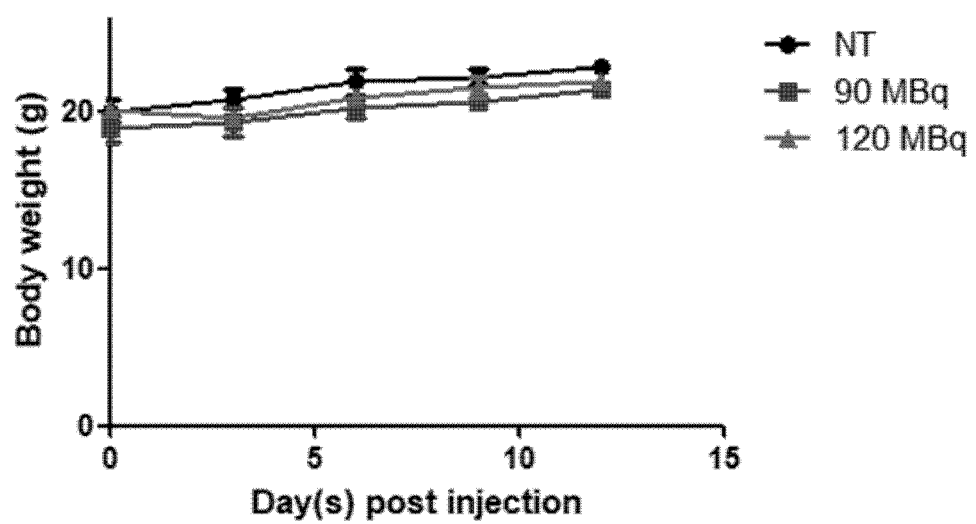
FIG. 3 is a graph showing the change in body weight over time when $^{177}$Lu-DOTA-NCS-DMPY2 according to an embodiment of the present invention was administered to a melanoma small animal model.

As a result of measuring the change in body weight of the experimental animals, as shown in FIG. 3, animals administered $^{177}$Lu-DOTA-NCS-DMPY2 according to an embodiment of the present invention showed no significant difference in body weight from the control group.

INDUSTRIAL AVAILABILITY

As described above, the radioactive compound according to an embodiment of the present invention can be very usefully used in the development of radioactive drugs for the treatment of melanoma.

The present invention has been described in more detail through the above-described Examples and Experimental Examples. However, the above Examples and Experimental Examples are intended to more fully describe the present invention, and it is obvious to those of ordinary skill in the art that the true scope of the present invention is not limited to the above Examples and Experimental Examples. Accordingly, the practical scope of protection of the present invention is determined as described in the following claims.

The invention claimed is:

1. A radioactive compound or a pharmaceutically acceptable salt thereof having the structure of Formula 1 or 2:

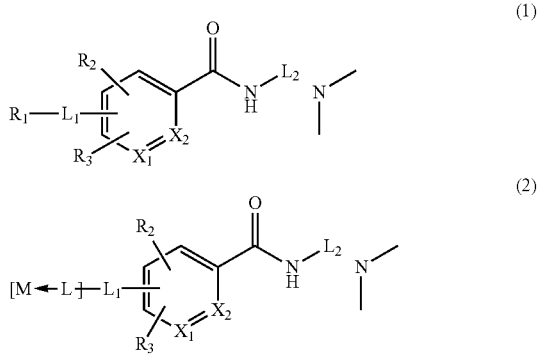

wherein X₁ and X₂ are each independently carbon or nitrogen nitrogen but at least on eof X₁ and X₂ is nitrogen;; L₁ is absent or a bond or a substituted or unsubstituted alkylene having 1 to 20 carbon atoms, a substituted or unsubstituted allyl having 6 to 14 carbon atoms, a substituted or unsubstituted heteroalkylene having 1 to 20 carbon atoms, a (poly)alkylene glycol having 2 to 60 carbon atoms, or one or more linkers linked modularly; $L_2$ is a bond or a substituted or unsubstituted alkylene group having 1 to 5 carbon atoms; $R_1$ is a radioactive isotope selected from the group consisting of $^{80m}Br$, $^{123}I$, $^{124}I$, $^{125}I$, $^{131}I$, and $^{32}P$ or a functional group containing the radioisotope and L is DOTA (1,4,7,10-tetraazacyclododecane-1,4,7,10-tetraacetic acid), DOTA-NCS, DOTA-NHS ester, DOTA-Bz-NCS, tris(t-bu)DOTA, HBED-CC-TFP ester, DTPA (Diethylene triamine pentaacetic acid), DO3A (1,4,7, 10-tetraazacyclododecane-1,4,7-triacetic acid), NOTA (1,4,7-triazacyclononane-1,4,7-triacetic acid), NODAGA (1,4,7-Triazacyclononane, 1-glutaric acid-4,7-acetic acid), TETA (1,4,8,11-tetraazacyclotetradecane -N,N',N'',N'''-tetraacetic acid), TE3A (1,4,8,11-tetraazacyclotetradecane-1,4,8-triacetic acid), TE2A (1,4,8,11-Tetraazabicyclohexadecane-4,11-diacetic acid), PCTA (3,6,9,15-tetraazabicyclo[9.3.1]pentadeca-1,11,13-triene-3,6,9,-triacetic acid), Cyclen, Cyclam or DFO (Deferrioxamine); M is a radioactive metal selected from the group consisting of $^{64}Cu$, $^{67}Cu$, $^{90}Cu$, $^{68}Ga$, $^{99}mTc$, $^{85}Sr$, $^{89}Sr$, $^{86}Y$, $^{90}Y$, $^{99}mTc$, $^{111}In$, $^{114m}In$, $^{149}Tb$, $^{152}Tb$, $^{153}Sm$, $^{163}Dy$, $^{166}Ho$, $^{169}Er$, $^{177}Lu$, $^{186}Re$, $^{188}Re$, $^{198}Au$, $^{211}At$, $^{212}Pb$, $^{223}Ra$, $^{224}Ra$, $^{225}Ac$ and $^{255}Fm$; and $R_2$ and $R_3$ are each independently hydrogen, a hydroxy group, an alkyl group having 1 to 3 carbon atoms, an acetamide group or an alkoxy having 1 to 3 carbon atoms, with a proviso that in Formula 2, $L_1$ is a substituted or unsubstituted alkylene having 1 to 20 carbon atoms, a substituted or unsubstituted allyl having 6 to 14 carbon atoms, a substituted or unsubstituted heteroalkylene having 1 to 20 carbon atoms, a (poly) alkylene glycol having 2 to 60 carbon atoms, or one or more linkers linked modularly.

2. The radioactive compound or an pharmaceutically acceptable salt of claim 1, wherein the linker is selected from the group consisting of a hydrophobic moiety for reducing hydrophilicity of the radioactive compound or a pharmaceutically acceptable salt thereof, an albumin-binding moiety for enhancing stability of the radioactive compound or a pharmaceutically acceptable salt and an in vivo clearance promoting moiety for clearing unbound radioactive compounds, which are added modularly.

3. The radioactive compound or an pharmaceutically acceptable salt of claim 2, wherein the hydrophobic moiety is selected from the group consisting of:

-continued

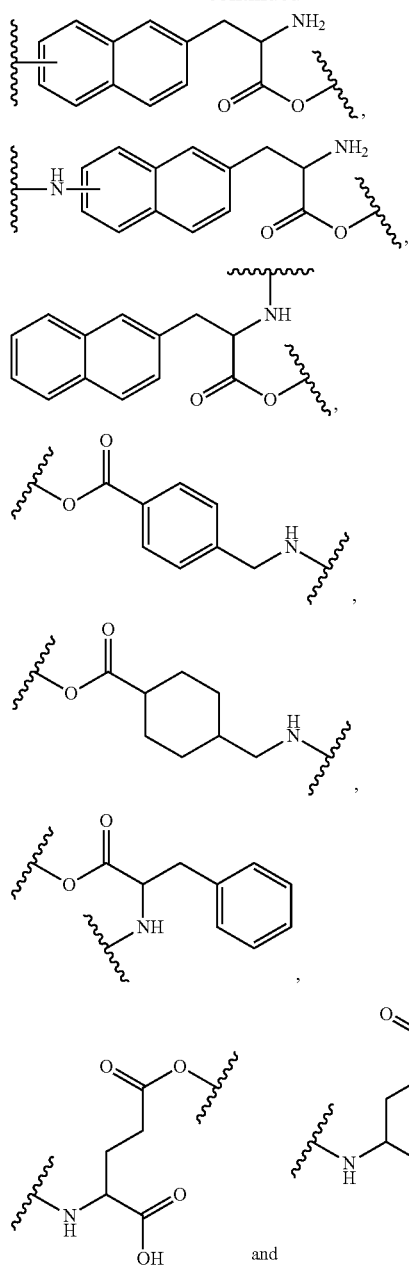

4. The radioactive compound or an pharmaceutically acceptable salt of claim 2, wherein the albumin-binding moiety is selected from the group consisting of:

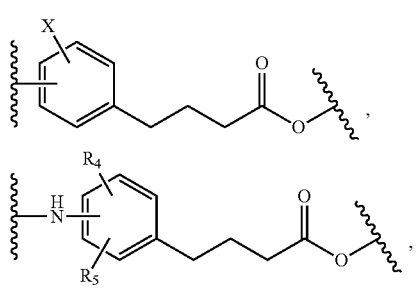

-continued

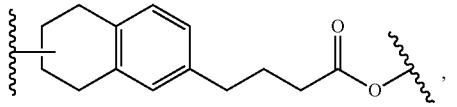

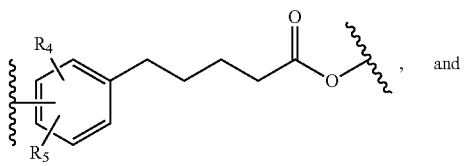

and

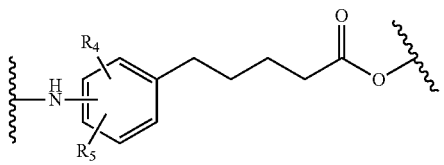

(wherein X is a halogen, $R_4$ and $R_5$ are independently hydrogen, hydroxy, or C1 to C6 alkyl or C1 to C6 alkoxy).

5. The radioactive compound or an pharmaceutically acceptable salt of claim 2, wherein the in vivo clearance promoting moiety is

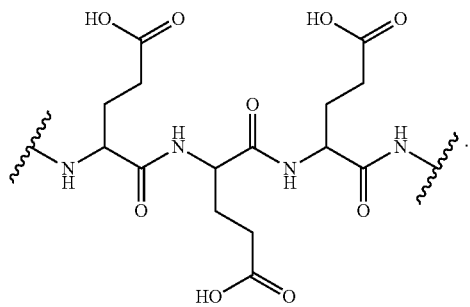 [SMILES: *NC(=O)C(CCC(=O)O)NC(=O)C(CCC(=O)O)NC(=O)C(CCC(=O)O)N*]

6. The radioactive compound or an pharmaceutically acceptable salt of claim 1, wherein the linker is selected from the group consisting of:

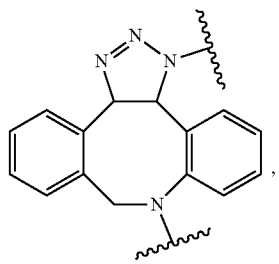

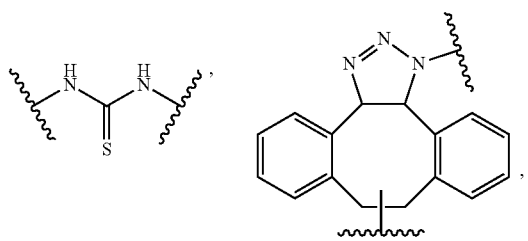

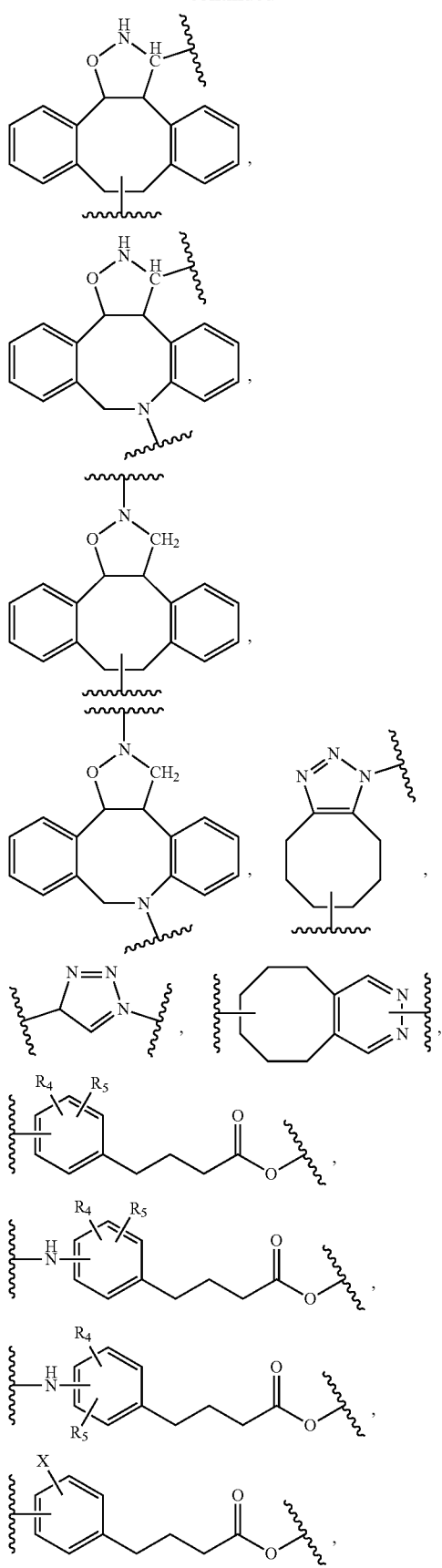
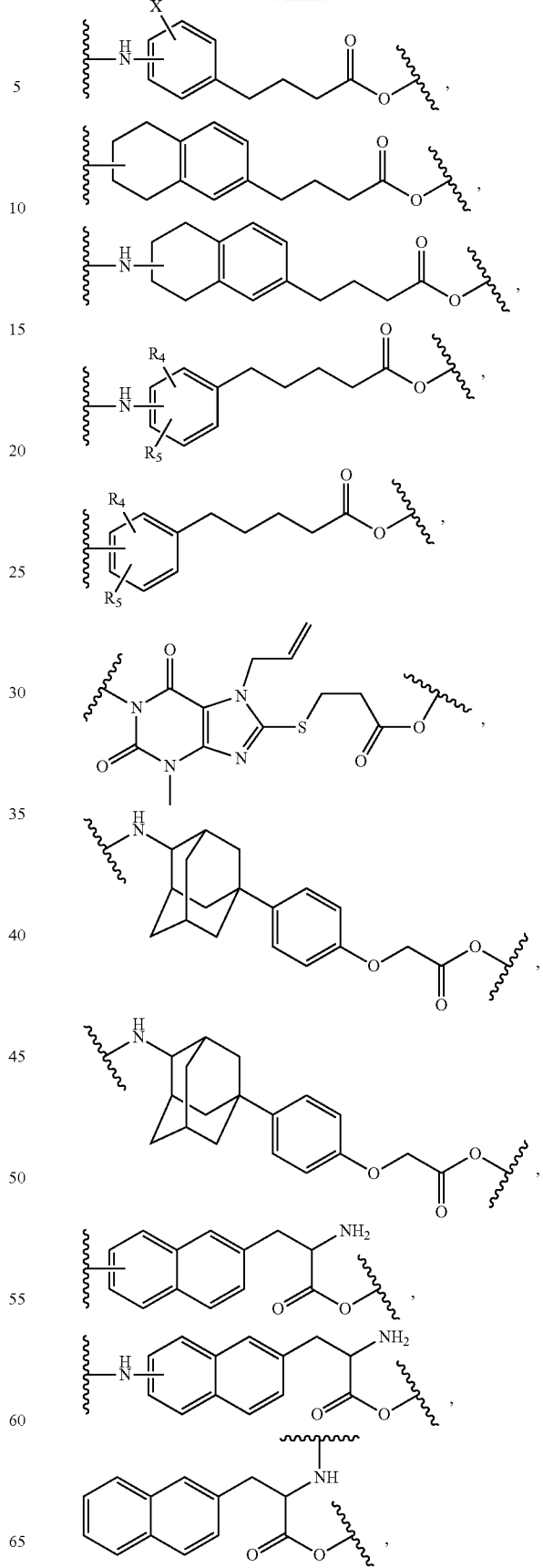

-continued

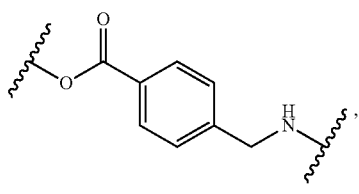,

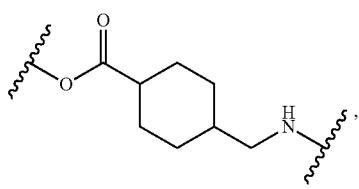,

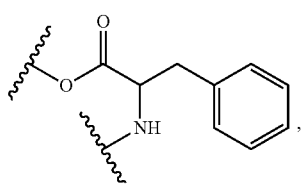,

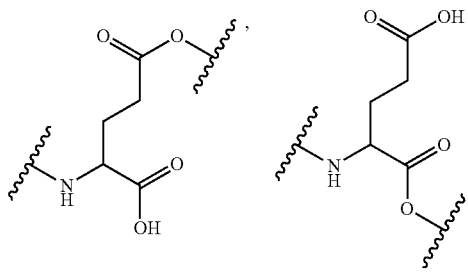 and

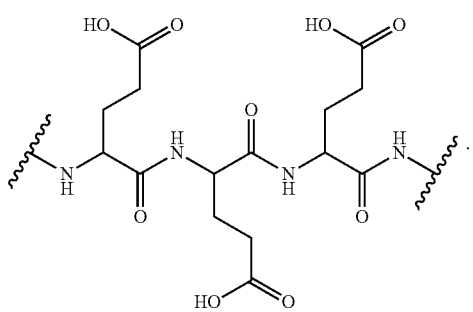.

7. The radioactive compound or an pharmaceutically acceptable salt of claim 1, wherein the bond of $L_1$ and $L_2$ is independently an ester bond, an amide bond, an ether bond, a thioether bond, a thioester bond, or a disulfide bond.

8. The radioactive compound or an pharmaceutically acceptable salt thereof of claim 1, wherein the compound is selected from the group consisting of:

(5-((2-(dimethylamino)ethyl)carbamoyl)pyridin-2-yl) carbamic [$^{131}$I] iodide

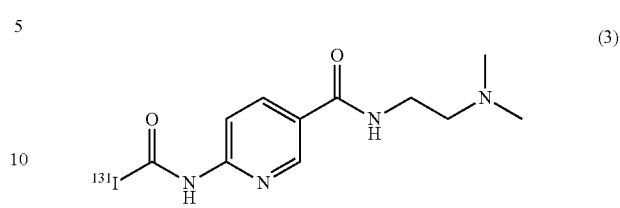

N-(2-(dimethylamino)ethyl)-6-([$^{125}$I] iodomethyl)nicotinamide

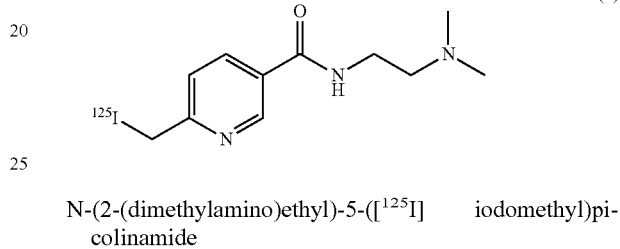

N-(2-(dimethylamino)ethyl)-5-([$^{125}$I] iodomethyl)picolinamide

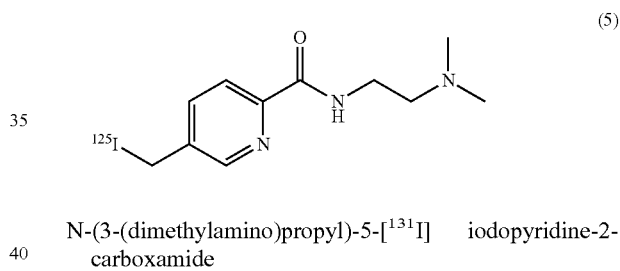

N-(3-(dimethylamino)propyl)-5-[$^{131}$I] iodopyridine-2-carboxamide

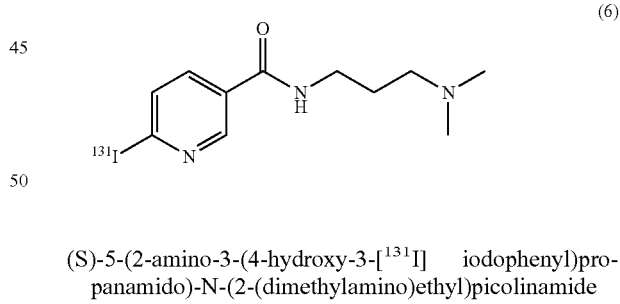

(S)-5-(2-amino-3-(4-hydroxy-3-[$^{131}$I] iodophenyl)propanamido)-N-(2-(dimethylamino)ethyl)picolinamide

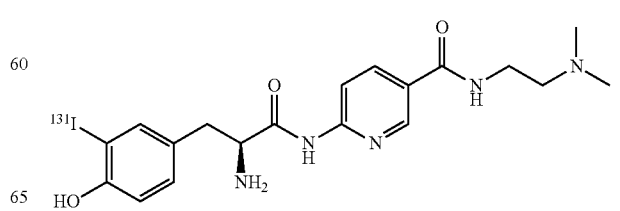

(S)-5-(4-(4-(2-(2-amino-3-(4-hydroxy-3-[$^{125}$I] iodophenyl)propanamido)ethyl)-1H-1,2,3-triazol-1-yl)butanamido)-N-(2-(dimethylamino)ethyl)picolinamide (8)
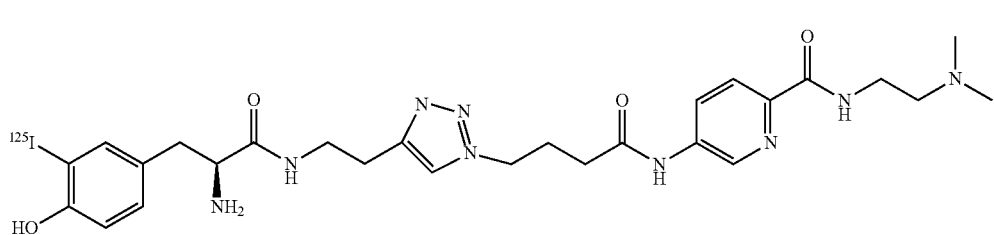

(S)-6-(6-(3-(3-(2-amino-3-(4-hydroxy-3-[$^{125}$I] iodophenyl)propanamido)propyl)-3H-dibenzo[b,f][1,2,3]triazolo[4,5-d]azocin-8 (9H)-yl)-6-oxohexanamido)-N-(2-(dimethylamino)ethyl) nicotinamide (9)
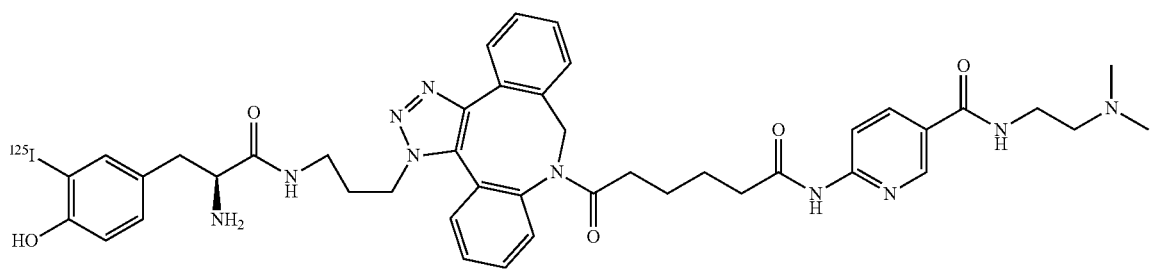

(6-((2-(dimethylamino)ethyl)carbamoyl)pyridin-3-yl) methyl dihydrogen [$^{32}$P]phosphate)

(10)
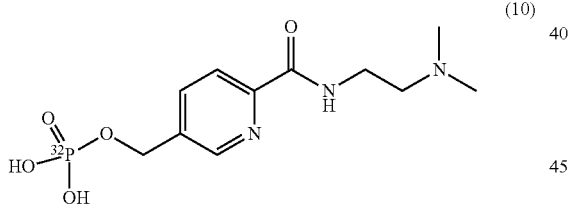

4-acetamido-N-(2-(dimethylamino)ethyl)-5-[$^{131}$I] iodo-2-methoxybenzamide

(11)
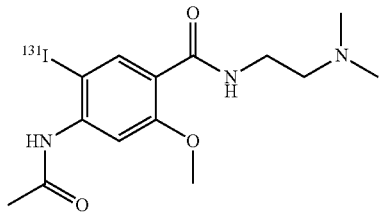

$^{177}$Lu-DOTA-DMPY2

-continued
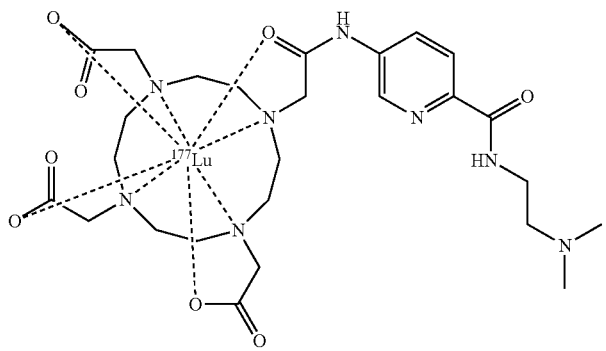
$^{177}$Lu-DOTA-NCS-DMPY2
(13)
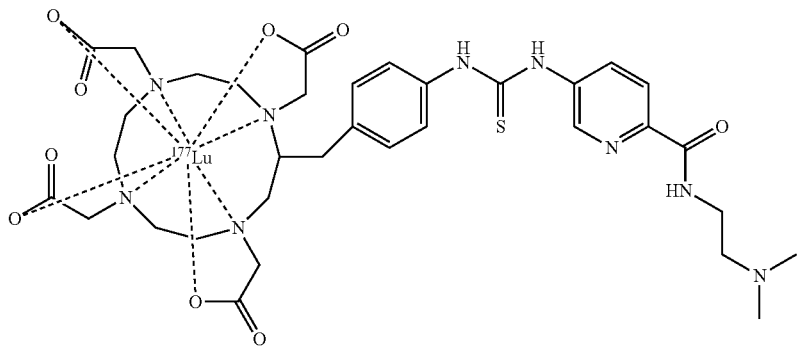
$^{177}$Lu-DOTA-NCS-triazole-PEG-DMPY2
(15)
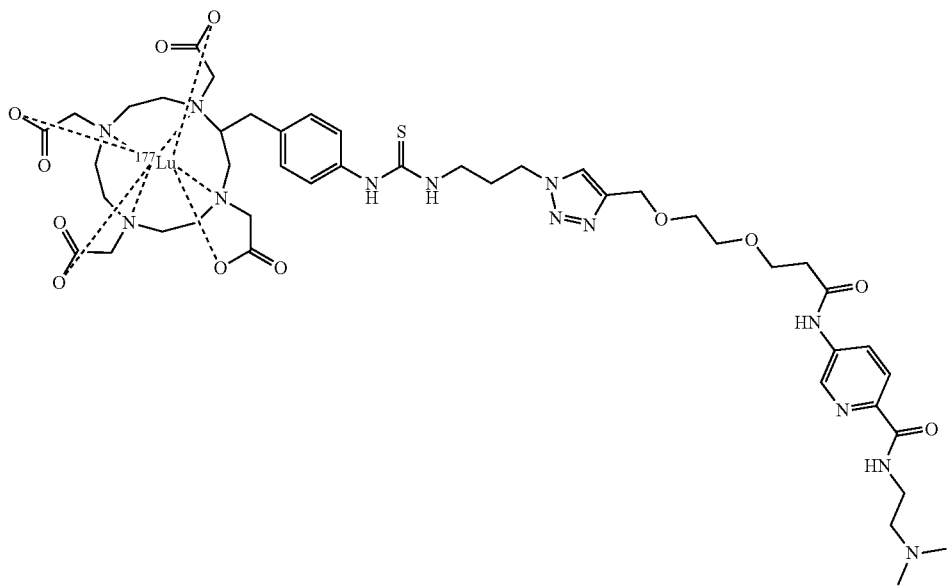
$^{177}$Lu-DOTA-NCS-ADIBO-DMPY2
(17)

-continued
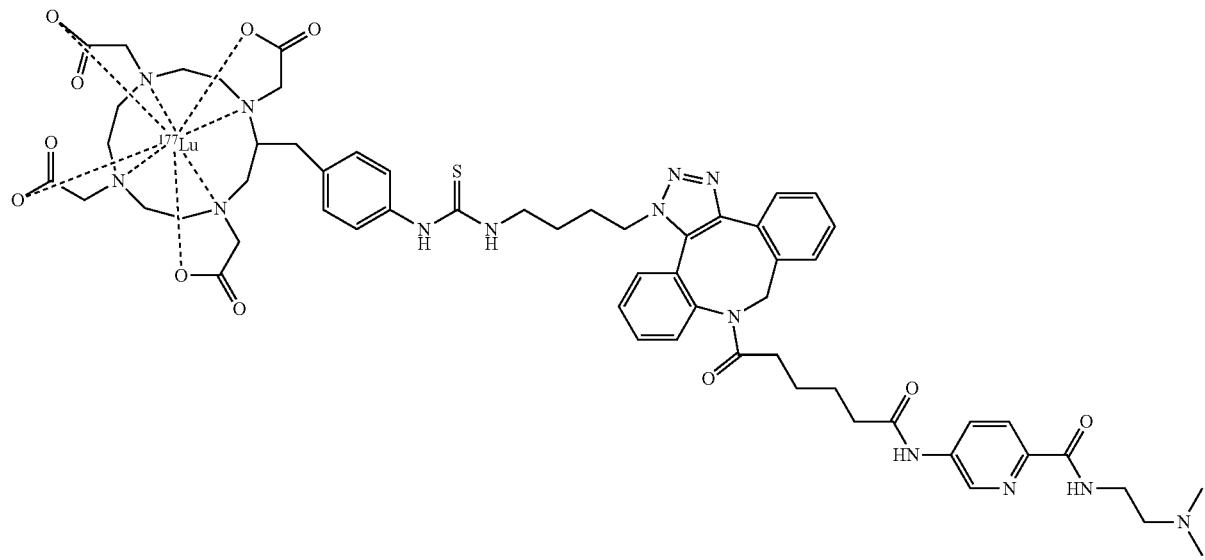
$^{177}$Lu-DOTA-Triazole-DMPY2
(19)
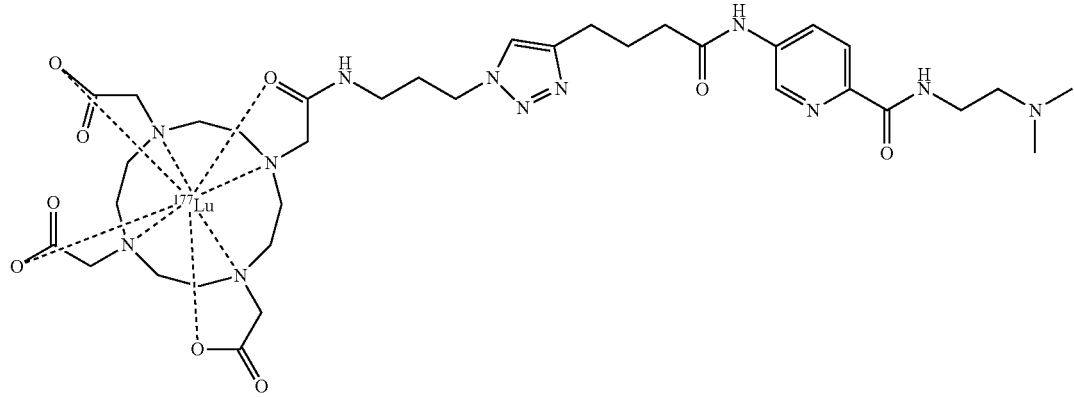
$^{177}$Lu-DOTA-Triazole-PEG-DMPY2
(21)
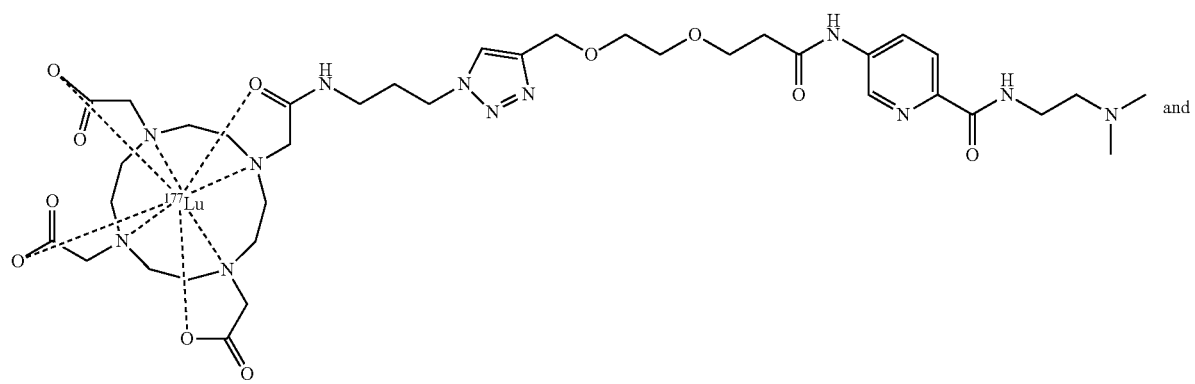
$^{177}$Lu-DOTA-ADIBO-DMPY2
(23)
and -continued

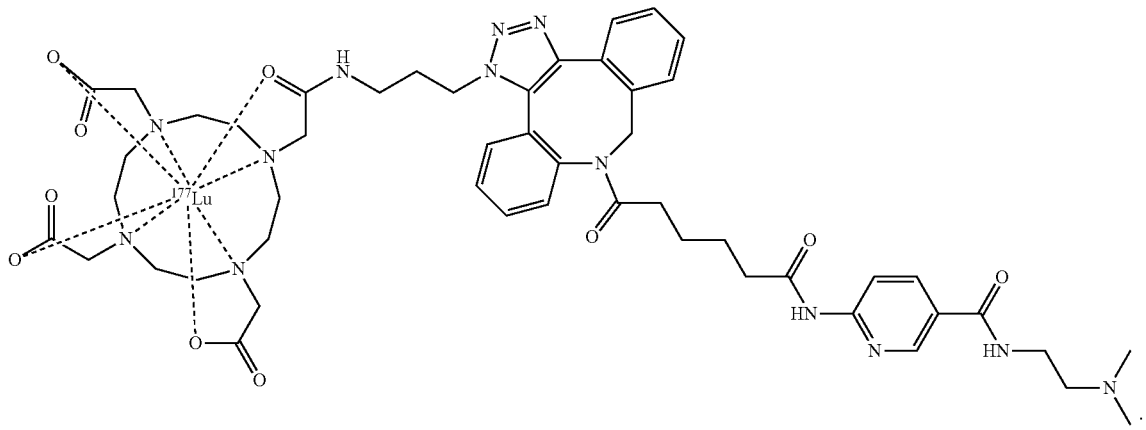

(25)

9. A pharmaceutical composition for treating melanoma comprising the radioactive compound of claim 1, or a pharmaceutically acceptable salt thereof as an active ingredient.

10. A pharmaceutical composition for treating melanoma comprising the radioactive compound of claim 3, or a pharmaceutically acceptable salt thereof as an active ingredient.

11. A pharmaceutical composition for treating melanoma comprising the radioactive compound of claim 4, or a pharmaceutically acceptable salt thereof as an active ingredient.

12. A pharmaceutical composition for treating melanoma comprising the radioactive compound of claim 5, or a pharmaceutically acceptable salt thereof as an active ingredient.

13. A pharmaceutical composition for treating melanoma comprising the radioactive compound of claim 6, or a pharmaceutically acceptable salt thereof as an active ingredient.

14. A pharmaceutical composition for treating melanoma comprising the radioactive compound of claim 7, or a pharmaceutically acceptable salt thereof as an active ingredient.

15. A pharmaceutical composition for treating melanoma comprising the radioactive compound of claim 8, or a pharmaceutically acceptable salt thereof as an active ingredient.

16. A method of treating melanoma in a subject in need thereof administering therapeutically effective amount of the radioactive compound or a pharmaceutically acceptable salt thereof of the claim 1.

\* \* \* \* \*